United States Patent
Karapetian et al.

(10) Patent No.: US 10,195,026 B2
(45) Date of Patent: Feb. 5, 2019

(54) MITRAL VALVE ANCHORING

(71) Applicant: Edwards Lifesciences Corporation, Irvine, CA (US)

(72) Inventors: Emil Karapetian, Huntington Beach, CA (US); Austin Bly, San Clemente, CA (US); Stanton J. Rowe, Newport Coast, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 212 days.

(21) Appl. No.: 14/802,922

(22) Filed: Jul. 17, 2015

(65) Prior Publication Data
US 2016/0022417 A1 Jan. 28, 2016

Related U.S. Application Data

(60) Provisional application No. 62/027,653, filed on Jul. 22, 2014.

(51) Int. Cl.
*A61F 2/24* (2006.01)

(52) U.S. Cl.
CPC .......... *A61F 2/2418* (2013.01); *A61F 2/2409* (2013.01); *A61F 2/2427* (2013.01);
(Continued)

(58) Field of Classification Search
CPC .... A61F 2/2445; A61F 2/2466; A61F 2/2418; A61F 2/2448; A61F 2220/0016
See application file for complete search history.

(56) References Cited

U.S. PATENT DOCUMENTS 3,409,013 A  11/1968  Berry
3,472,230 A  10/1969  Fogarty
(Continued)

FOREIGN PATENT DOCUMENTS

DE   2246526 A1   3/1973
DE   19532846 A1   3/1997
(Continued)

OTHER PUBLICATIONS

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

(Continued)

*Primary Examiner* — Thomas J Sweet
*Assistant Examiner* — Tiffany Shipmon
(74) *Attorney, Agent, or Firm* — Klarquist Sparkman LLP

(57) ABSTRACT

Disclosed herein are prosthetic devices and related methods for implantation at the native mitral valve of the heart by drawing an atrial portion and a ventricular portion toward each other from opposite sides of the native mitral valve, clamping the native mitral valve therebetween. One or more retention members passing through the mitral valve orifice or through a puncture in the native valve anatomy can couple the atrial and ventricular members together and keep them anchored onto the native mitral valve anatomy. The atrial portion can seat against the atrial side of the mitral annulus while the ventricular portion can include hooks and/or a sub-annular ring that engage and capture the native mitral valve apparatus to provide anchorage. The described technology can avoid the need to use sutures to anchor a prosthetic device at the mitral valve region.

6 Claims, 26 Drawing Sheets

(52) U.S. Cl.
CPC ..... *A61F 2/2457* (2013.01); *A61F 2210/0014* (2013.01); *A61F 2220/0008* (2013.01); *A61F 2220/0033* (2013.01); *A61F 2220/0041* (2013.01); *A61F 2230/0034* (2013.01); *A61F 2250/006* (2013.01)

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,037,434 A | 8/1991 | Lane |
| 5,047,041 A | 9/1991 | Sammuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,522 A | 5/1995 | Trott |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,906,619 A | 5/1999 | Olson et al. |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson, IV et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,306,141 B1 | 10/2001 | Jervis |
| 6,312,465 B1 | 11/2001 | Griffin et al. |
| 6,350,277 B1 | 2/2002 | Kocur |
| 6,379,372 B1 | 4/2002 | Dehdashtian et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,527,979 B2 | 3/2003 | Constantz |
| 6,569,196 B1 | 5/2003 | Vesely et al. |
| 6,575,959 B1 | 6/2003 | Sarge et al. |
| 6,582,462 B1 | 6/2003 | Andersen et al. |
| 6,605,112 B1 | 8/2003 | Moll |
| 6,730,118 B2 | 5/2004 | Spenser et al. |
| 6,733,525 B2 | 5/2004 | Yang et al. |
| 6,790,229 B1 | 9/2004 | Berreklouw |
| 6,830,584 B1 | 12/2004 | Seguin |
| 6,893,460 B2 | 5/2005 | Spenser et al. |
| 6,908,481 B2 | 6/2005 | Cribier |
| 6,974,476 B2 | 12/2005 | McGuckin, Jr. et al. |
| 7,018,406 B2 | 3/2006 | Seguin et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,381,210 B2 | 6/2008 | Zarbatany et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |

(56) References Cited

U.S. PATENT DOCUMENTS

| | | |
|---|---|---|
| 7,462,191 B2 | 12/2008 | Spenser et al. |
| 7,510,575 B2 | 3/2009 | Spenser et al. |
| 7,524,330 B2 | 4/2009 | Berreklouw |
| 7,530,253 B2 | 5/2009 | Spenser et al. |
| 7,579,381 B2 | 8/2009 | Dove |
| 7,585,321 B2 | 9/2009 | Cribier |
| 7,618,446 B2 | 11/2009 | Andersen et al. |
| 7,621,948 B2 | 11/2009 | Herrmann et al. |
| 7,704,222 B2 | 4/2010 | Wilk et al. |
| 7,736,327 B2 | 6/2010 | Wilk et al. |
| 7,892,281 B2 | 2/2011 | Seguin et al. |
| 7,914,575 B2 | 3/2011 | Guyenot et al. |
| 7,993,394 B2 | 8/2011 | Hariton et al. |
| 8,007,992 B2 | 8/2011 | Tian et al. |
| 8,029,556 B2 | 10/2011 | Rowe |
| 8,092,521 B2 | 1/2012 | Figulla et al. |
| 8,118,866 B2 | 2/2012 | Herrmann et al. |
| 8,167,932 B2 | 5/2012 | Bourang |
| 8,206,437 B2 | 6/2012 | Bonhoeffer et al. |
| 8,216,174 B2 | 7/2012 | Wilk et al. |
| 8,317,858 B2 | 11/2012 | Straubinger et al. |
| 8,398,704 B2 | 3/2013 | Straubinger et al. |
| 8,416,643 B2 | 4/2013 | Magee |
| 8,449,599 B2 | 5/2013 | Chau et al. |
| 8,460,370 B2 | 6/2013 | Zakay |
| 8,475,525 B2 | 7/2013 | Maisano et al. |
| 2001/0021872 A1 | 9/2001 | Bailey et al. |
| 2002/0032481 A1 | 3/2002 | Gabbay |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0039436 A1 | 2/2004 | Spenser et al. |
| 2004/0092858 A1 | 5/2004 | Wilson et al. |
| 2004/0133263 A1 | 7/2004 | Dusbabek et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0137688 A1 | 6/2005 | Salahieh et al. |
| 2005/0137698 A1 | 6/2005 | Salahieh et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2005/0288766 A1 | 12/2005 | Plain et al. |
| 2006/0025857 A1 | 2/2006 | Bergheim et al. |
| 2006/0058872 A1 | 3/2006 | Salahieh et al. |
| 2006/0142837 A1 | 6/2006 | Haverkost et al. |
| 2006/0149350 A1 | 7/2006 | Patel et al. |
| 2006/0161249 A1 | 7/2006 | Realyvasquez et al. |
| 2006/0195134 A1 | 8/2006 | Crittenden |
| 2006/0229719 A1 | 10/2006 | Marquez et al. |
| 2006/0241745 A1 | 10/2006 | Solem |
| 2006/0259135 A1 | 11/2006 | Navia et al. |
| 2006/0259137 A1 | 11/2006 | Artof et al. |
| 2006/0276874 A1 | 12/2006 | Wilson et al. |
| 2007/0005131 A1 | 1/2007 | Taylor |
| 2007/0010877 A1 | 1/2007 | Salahieh et al. |
| 2007/0027534 A1 | 2/2007 | Bergeim et al. |
| 2007/0066863 A1 | 3/2007 | Rafiee et al. |
| 2007/0088431 A1 | 4/2007 | Bourang et al. |
| 2007/0100439 A1 | 5/2007 | Cangialosi et al. |
| 2007/0112422 A1 | 5/2007 | Dehdashtian |
| 2007/0142906 A1 | 6/2007 | Figulla et al. |
| 2007/0156224 A1 | 7/2007 | Cioanta et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0270943 A1 | 11/2007 | Solem |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082166 A1 | 4/2008 | Styrc et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0161911 A1 | 7/2008 | Revuelta et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2009/0005863 A1 | 1/2009 | Goetz et al. |
| 2009/0054968 A1 | 2/2009 | Bonhoeffer et al. |
| 2009/0054974 A1 | 2/2009 | McGuckin, Jr. et al. |
| 2009/0076598 A1 | 3/2009 | Salahieh et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292353 A1 | 11/2009 | Yoganathan et al. |
| 2009/0319037 A1 | 12/2009 | Rowe et al. |
| 2010/0016958 A1 | 1/2010 | St. Goar et al. |
| 2010/0049313 A1 | 2/2010 | Alon et al. |
| 2010/0131054 A1 | 5/2010 | Tuval et al. |
| 2010/0137979 A1 | 6/2010 | Tuval et al. |
| 2010/0174362 A1 | 7/2010 | Straubinger et al. |
| 2010/0204781 A1 | 8/2010 | Alkhatib |
| 2010/0217382 A1 | 8/2010 | Chau et al. |
| 2010/0262231 A1 | 10/2010 | Tuval et al. |
| 2011/0015616 A1 | 1/2011 | Straubinger et al. |
| 2011/0015729 A1 | 1/2011 | Jimenez et al. |
| 2011/0137397 A1 | 6/2011 | Chau et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0238159 A1 | 9/2011 | Guyenot et al. |
| 2011/0288634 A1 | 11/2011 | Tuval et al. |
| 2011/0319989 A1 | 12/2011 | Lane et al. |
| 2012/0035722 A1 | 2/2012 | Tuval |
| 2012/0046741 A1 | 2/2012 | Tuval et al. |
| 2012/0046742 A1 | 2/2012 | Tuval et al. |
| 2012/0101570 A1 | 4/2012 | Tuval et al. |
| 2012/0123529 A1 | 5/2012 | Levi et al. |
| 2012/0165930 A1 | 6/2012 | Gifford, III et al. |
| 2012/0185039 A1 | 7/2012 | Tuval et al. |
| 2012/0197386 A1 | 8/2012 | Von Segesser et al. |
| 2012/0209374 A1 | 8/2012 | Bonhoeffer et al. |
| 2012/0283823 A1 | 11/2012 | Bonhoeffer et al. |
| 2012/0296418 A1 | 11/2012 | Bonyuet et al. |
| 2012/0310336 A1 | 12/2012 | Figulla et al. |
| 2012/0323317 A1* | 12/2012 | Karapetian ........... A61F 2/2409 623/2.37 |
| 2013/0073035 A1 | 3/2013 | Tuval et al. |
| 2013/0079869 A1 | 3/2013 | Straubinger et al. |
| 2013/0166022 A1 | 6/2013 | Conklin |
| 2013/0190861 A1 | 7/2013 | Chau et al. |
| 2013/0190862 A1 | 7/2013 | Pintor et al. |
| 2013/0197622 A1 | 8/2013 | Mitra et al. |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10010074 A1 | 10/2001 |
| DE | 10049812 A1 | 4/2002 |

(56) References Cited

FOREIGN PATENT DOCUMENTS

| | | |
|---|---|---|
| DE | 10049813 C1 | 4/2002 |
| DE | 10049814 A1 | 4/2002 |
| DE | 10049815 A1 | 4/2002 |
| DE | 102006052564 B3 | 12/2007 |
| EP | 0103546 A1 | 3/1984 |
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1469797 A1 | 10/2004 |
| EP | 1570809 A1 | 9/2005 |
| EP | 1653888 A2 | 5/2006 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 91/17720 A1 | 11/1991 |
| WO | 92/17118 A1 | 10/1992 |
| WO | 93001768 A1 | 2/1993 |
| WO | 97/24080 A1 | 7/1997 |
| WO | 98/29057 A1 | 7/1998 |
| WO | 99/33414 A1 | 7/1999 |
| WO | 99/40964 A1 | 8/1999 |
| WO | 99/47075 A1 | 9/1999 |
| WO | 00/18333 A1 | 4/2000 |
| WO | 00/41652 A1 | 7/2000 |
| WO | 00/47139 A1 | 8/2000 |
| WO | 0128459 A1 | 4/2001 |
| WO | 01/35878 A2 | 5/2001 |
| WO | 01/49213 A2 | 7/2001 |
| WO | 01/62189 A1 | 8/2001 |
| WO | 0154624 A1 | 8/2001 |
| WO | 0154625 A1 | 8/2001 |
| WO | 01/64137 A1 | 9/2001 |
| WO | 01/76510 A2 | 10/2001 |
| WO | 02/22054 A1 | 3/2002 |
| WO | 02/36048 A1 | 5/2002 |
| WO | 02/41789 A2 | 5/2002 |
| WO | 02/43620 A1 | 6/2002 |
| WO | 02/47575 A2 | 6/2002 |
| WO | 02/49540 A2 | 6/2002 |
| WO | 03/047468 A1 | 6/2003 |
| WO | 05/034812 | 4/2005 |
| WO | 05/087140 A1 | 9/2005 |
| WO | 05/102015 | 11/2005 |
| WO | 06/014233 A2 | 2/2006 |
| WO | 06/034008 A2 | 3/2006 |
| WO | 06/108090 | 10/2006 |
| WO | 06/111391 | 10/2006 |
| WO | 06/138173 | 12/2006 |
| WO | 08/005405 A2 | 1/2008 |
| WO | 08/035337 A2 | 3/2008 |
| WO | 08/147964 A1 | 3/2008 |
| WO | 08/150529 A1 | 12/2008 |
| WO | 09/024859 | 2/2009 |
| WO | 09/116041 | 9/2009 |
| WO | 2013128432 A1 | 9/2013 |

OTHER PUBLICATIONS

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.
Al Zaibag, Muayed, et al., "Percutaneous Balloon Valvotomy in Tricuspid Stenosis," British Heart Journal, Jan. 1987, vol. 57, No. 1, pp. 51-53.
Andersen, et al., "Transluminal implantation of artificial heart valves. Description of a new expandable aortic valve and initial results with implantation by catheter technique in closed chest pigs." European Heart Journal (1992), 13, 704-708.
Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.
Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.
Dake, Transluminal Placement of Endovascular Stent-Grafts for the Treatment of Descending Thoracic Aortic Aneurysms, New Engl. J.Med., 1994; 331:1729 34.
Dotter, M.D., Charles T., "Transluminal Treatment of Arteriosclerotic Obstruction," University of Oregon's Minthom Memorial Laboratory for Cardiovascular Research through Radiology, Circulation, vol. XXX, Nov. 1964, pp. 654-670.
Kolata, Gina, "Device That Opens Clogged Arteries Gets a Failing Grade in a New Study," nytimes.com, http://www.nytimes.com/1991/01/03/health/device-that-opens-clogged-arteries-gets-a-faili . . . , Jul. 29, 2009, 2 pages.
Inoue, M.D., Kanji, et al., "Clinical Application of Transvenous Mitral Commissurotomy by a New Balloon Catheter," The Journal of Thoracic and Cardiovascular Surgery 87:394-402, 1984.
Lawrence, Jr., M.D., David D., "Percutaneous Endovascular Graft: Experimental Evaluation," Radiology 1897; 163: 357-360.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Porstmann, W., et al., "Der Verschluß des Ductus Arteriosus Persistens ohne Thorakotomie," Thoraxchirurgie Vaskuläre Chirurgie, Band 15, Heft 2, Stuttgart, im Apr. 1967, pp. 199-203.
Rashkind, M.D., William J., "Creation of an Atrial Septal Defect Withoput Thoracotomy," the Journal of the American Medical Association, vol. 196, No. 11, Jun. 13, 1966, pp. 173-174.
Rashkind, M.D., William J., "Historical Aspects of Interventional Cardiology: Past, Present, Future," Texas Heart Institute Journal, Interventional Cardiology, pp. 363-367.
Rösch, M.D., Josef, "The Birth, Early Years and Future of Interventional Radiology," J Vasc Interv Radiol 2003; 14:841-853.
Ross, F.R.C.S., D.N., "Aortic Valve Surgery," Guy's Hospital, London, pp. 192-197, approximately 1968.
Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.
Selby, M.D., J. Bayne, "Experience with New Retrieval Forceps for Foreign Body Removal in the Vascular, Urinary, and Biliary Systems," Radiology 1990; 176:535-538.
Serruys, P.W., et al., "Stenting of Coronary Arteries. Are we the Sorcerer's Apprentice?," European Heart Journal (1989) 10, 774-782, pp. 37-45, Jun. 13, 1989.
Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.
Uchida, Barry T., et al., "Modifications of Gianturco Expandable Wire Stents," AJR:150, May 1988, Dec. 3, 1987, pp. 1185-1187.
Urban, M.D., Philip, "Coronary Artery Stenting," Editions Médecine et Hygiène, Genève, 1991, pp. 5-47.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.
Wheatley, M.D., David J., "Valve Prostheses," Rob & Smith's Operative Surgery, Fourth Edition, pp. 415-424, Butterworths 1986.
Int'l. Search Report for PCT/US2015/041369, dated Oct. 26, 2015.
Supplementary Search Report issued in EP15825014.2, completed Jul. 5, 2017.

\* cited by examiner

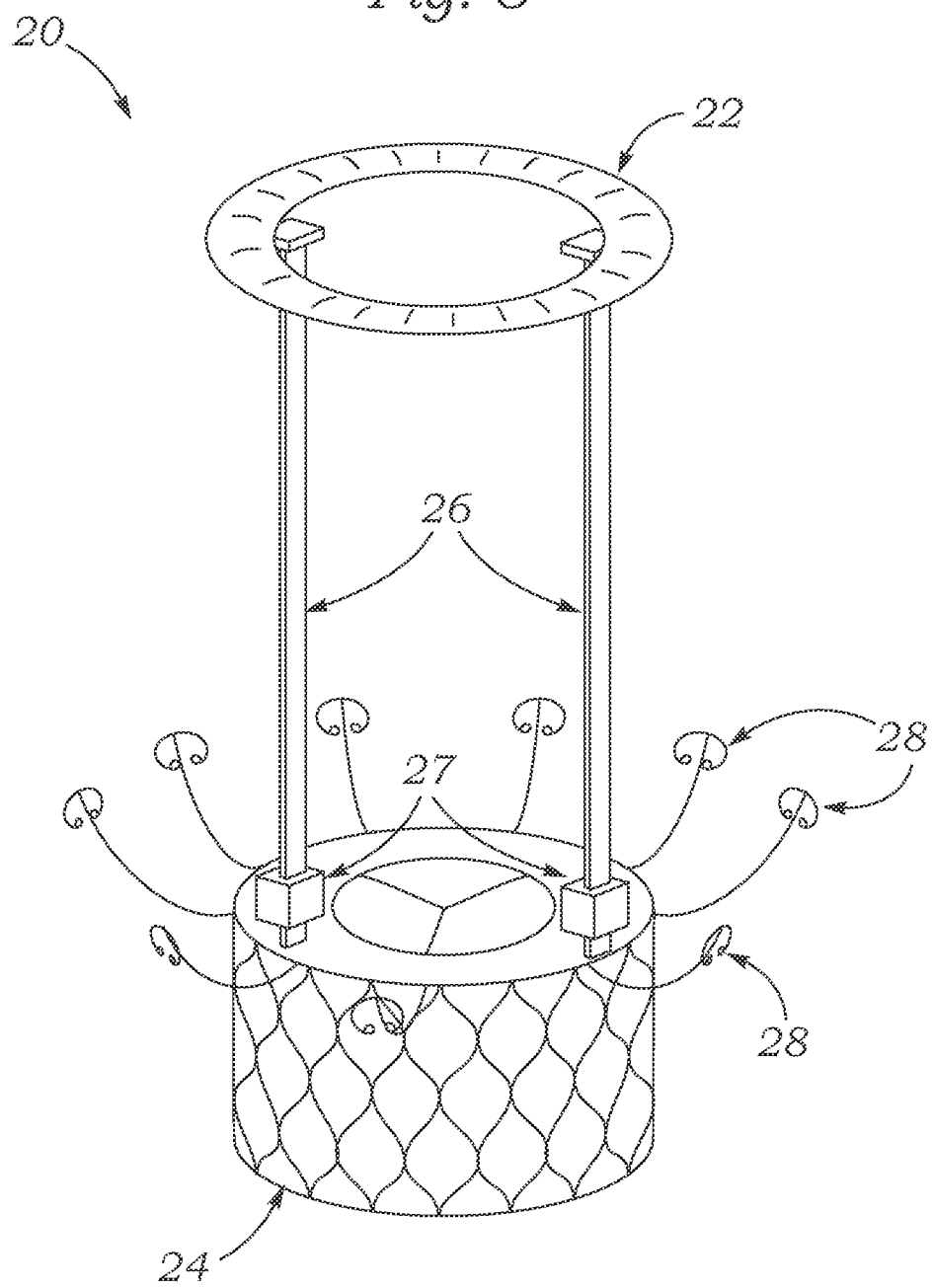

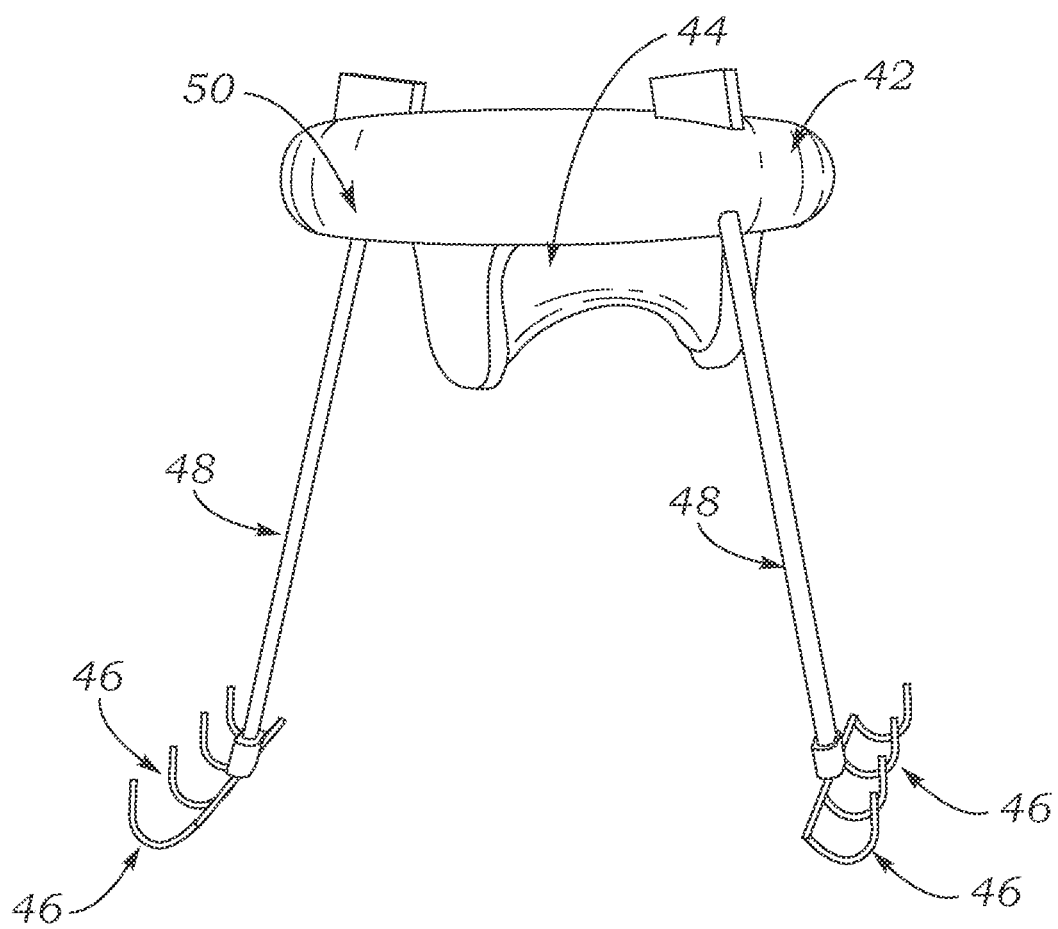

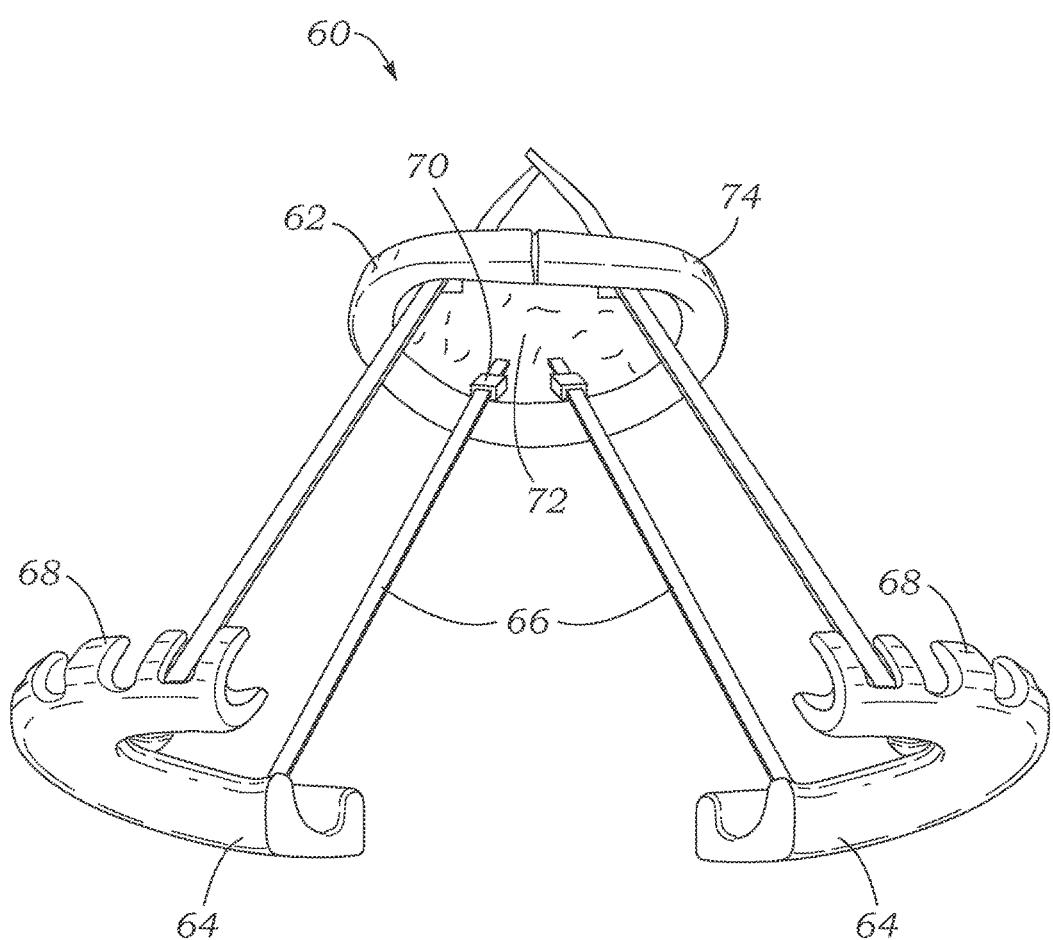

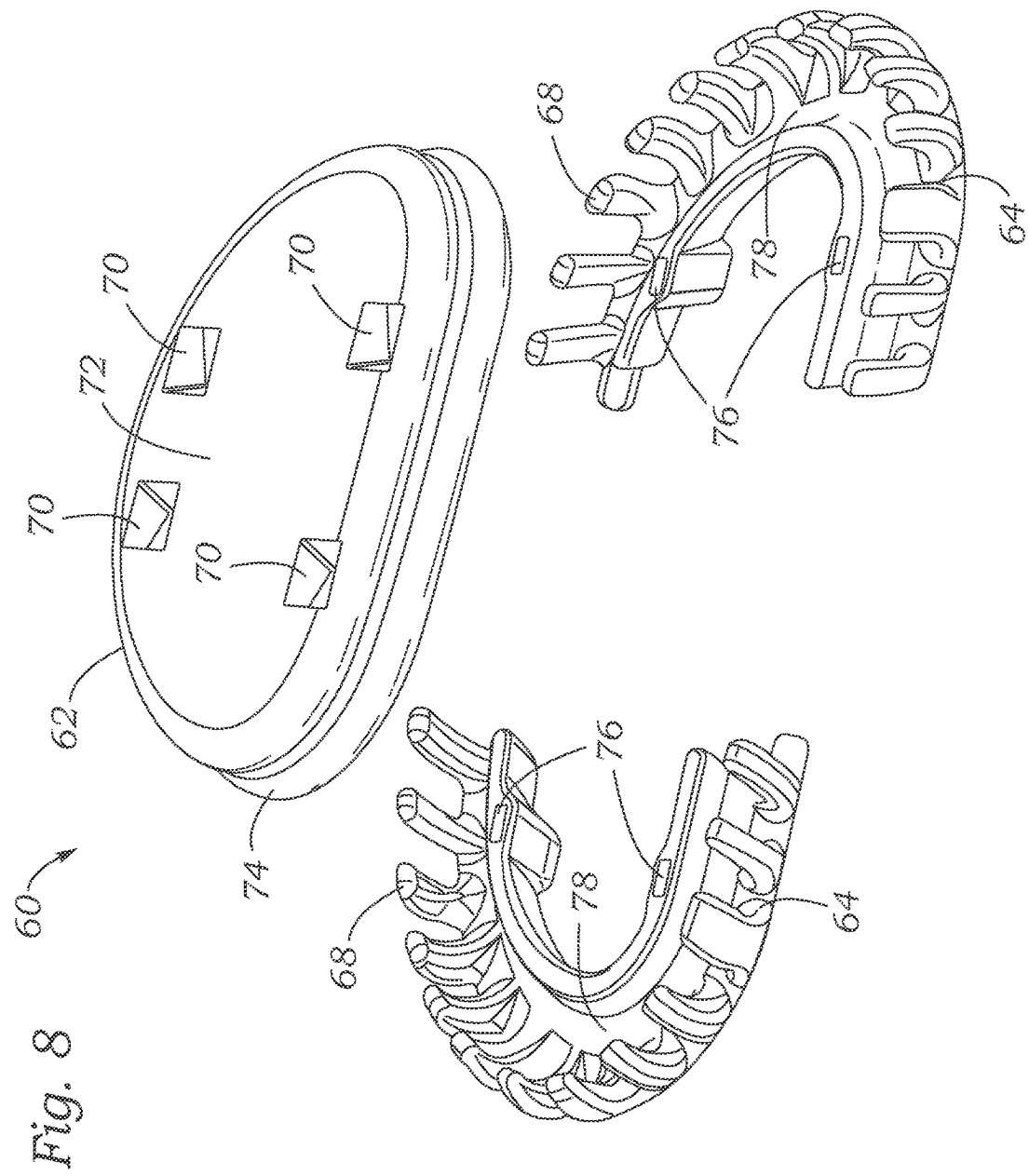

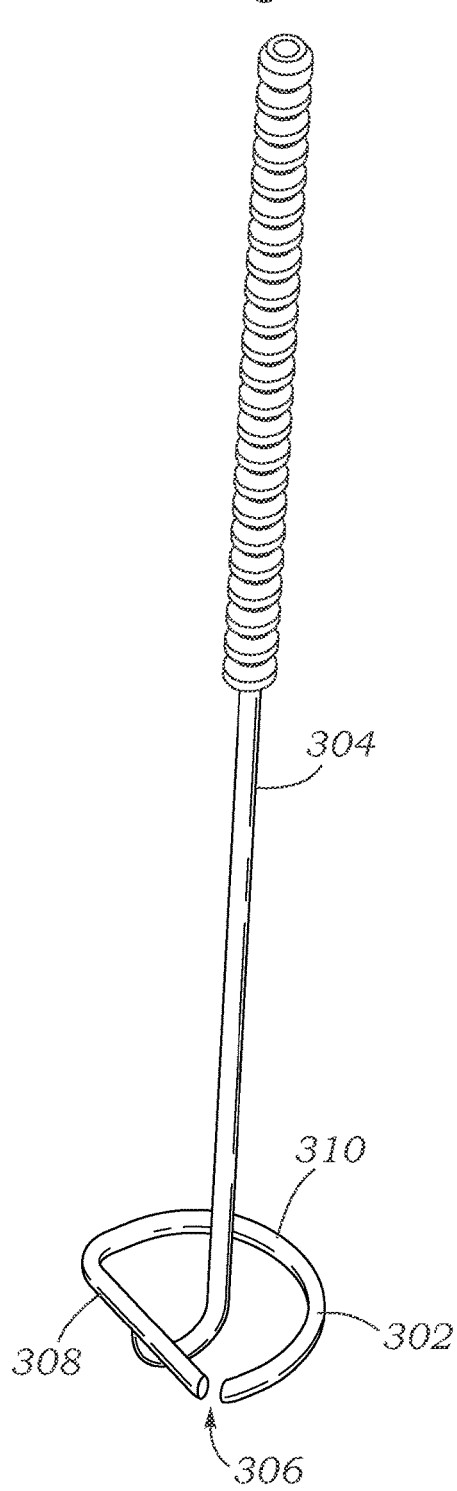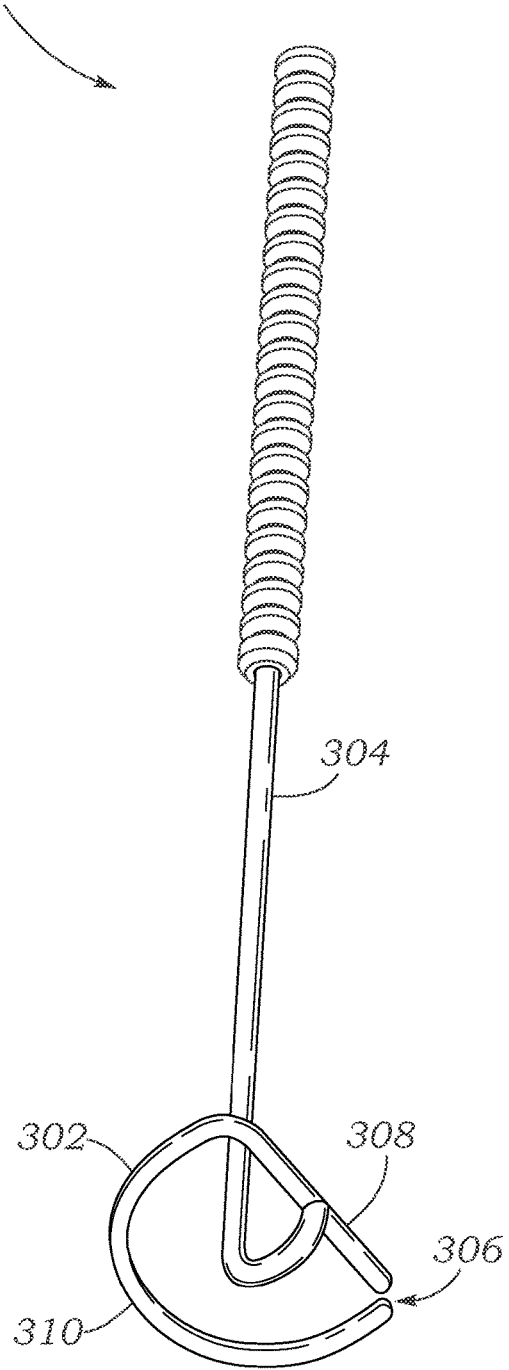

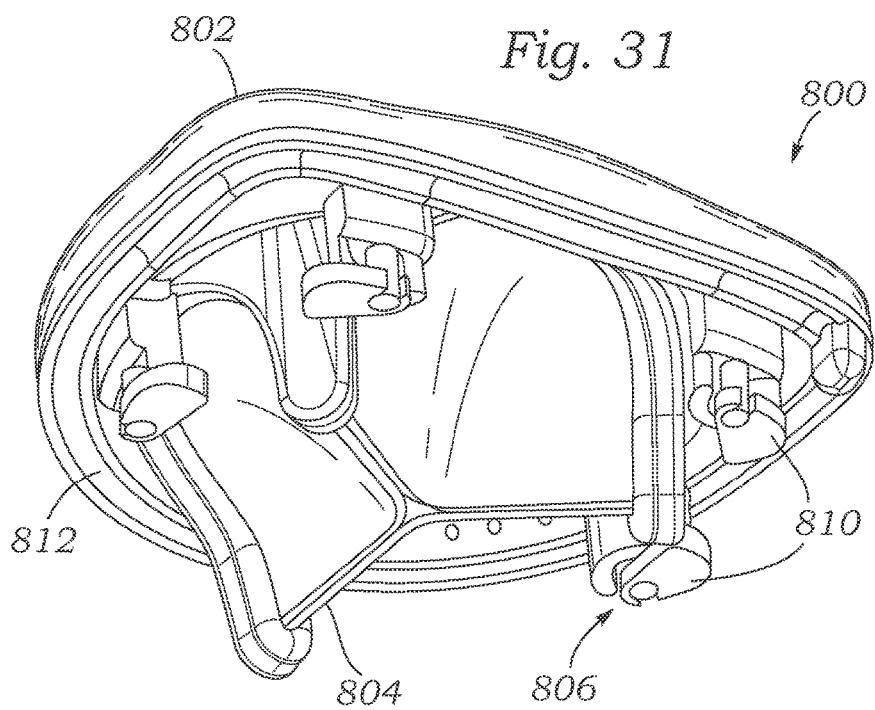
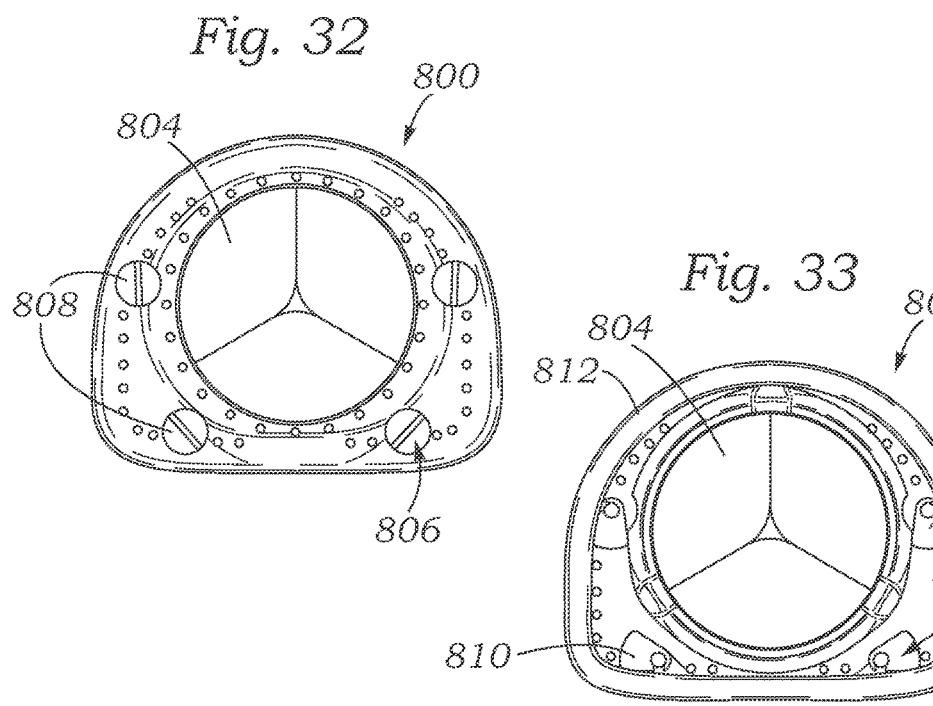

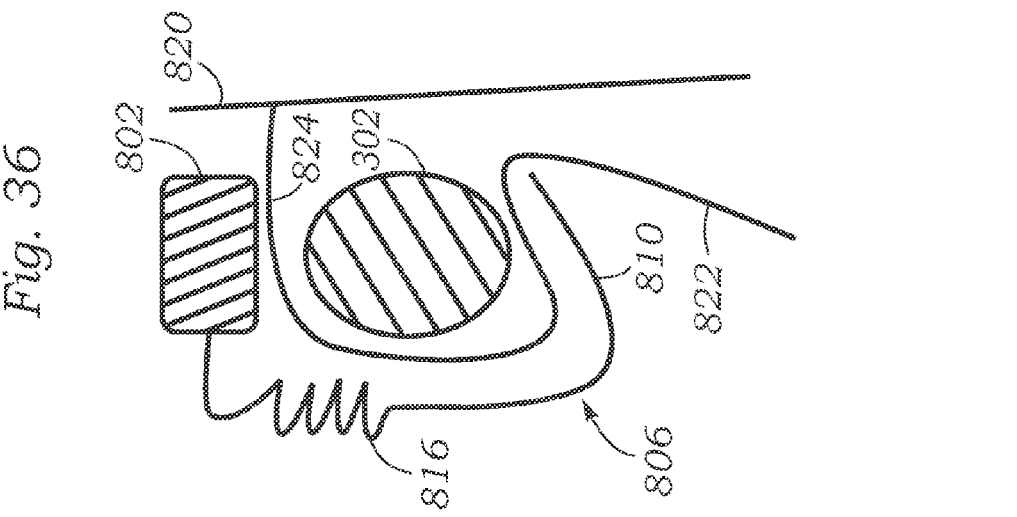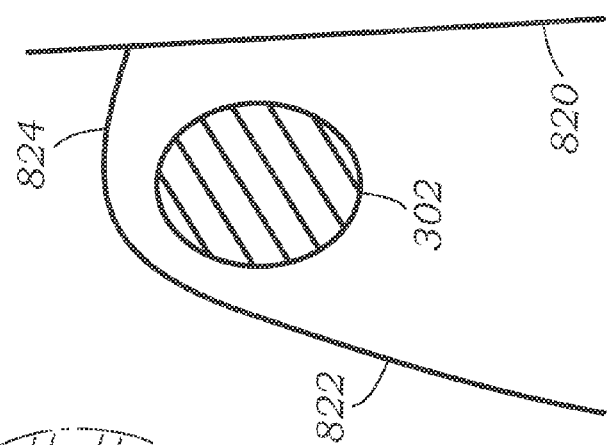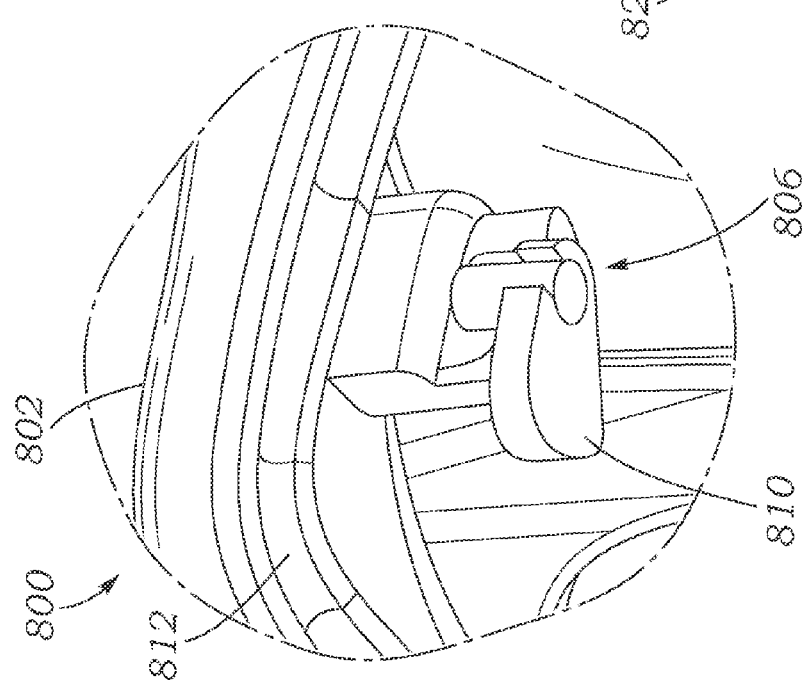

MITRAL VALVE ANCHORING

CROSS-REFERENCE TO RELATED APPLICATION

This application claims the benefit of U.S. Provisional Application Ser. No. 62/027,653 filed on Jul. 22, 2014, which is incorporated by reference herein in its entirety.

FIELD

This application is related to devices and methods for anchoring a prosthetic structure at the mitral valve.

BACKGROUND

Anchoring prosthetic devices at native heart valve locations is commonly performed by suturing the devices directly to nearby tissue of the heart or by expanding the device radially outwardly against the surrounding tissue, such as via a transcatheter delivery.

SUMMARY

Disclosed herein are devices and methods for anchoring a prosthetic mitral valve or similar devices at the native mitral valve region of the heart that clamp a native mitral valve structure between an atrial portion and a ventricular portion disposed on opposite sides of the native mitral valve structure, the atrial portion and ventricular portion pulled towards each other by tension and/or another force. The described technology can eliminate the need to use sutures to anchor a prosthetic device at the mitral valve region.

Exemplary prosthetic mitral valves disclosed herein comprise an atrial portion for placement in the left atrium, a ventricular portion for placement in the left ventricle, and at least one retention member that couples the atrial portion to the ventricular portion through the mitral valve orifice. Either the atrial portion or the ventricular portion can include a prosthetic valve structure that is positioned within the mitral valve orifice to replace the functionality of the native mitral valve. In some embodiments, the ventricular portion can include hooks or other features configured to extend behind the native mitral leaflets in order to anchor the device at the ventricular side of the mitral valve, while the atrial portion can be seated along the atrial side of the mitral valve annulus. The length of the retention member(s) between the atrial portion and the ventricular portion can be shortened to reduce a distance between the atrial portion and the ventricular portion such that the atrial portion and the ventricular portion move toward each other and become engaged on opposite sides of the native mitral annulus using tension or other clamping force from the retention members to anchor the prosthetic mitral valve. In some such procedures, no sutures are needed to anchor the prosthetic device.

In some embodiments, the ventricular portion comprises a single member, such as an annular or semi-annular body. In some such embodiments, the ventricular portion includes an annular frame with a prosthetic valve structure mounted within the frame and hooks extending from the frame for engaging the native valve structure. In some embodiments, the ventricular portion includes a generally D-shaped ring that is broken at one location, such that a free edge of a native leaflet can be inserted into the ring through the break, allowing the D-shaped ring to be rotated around behind the native leaflets and chordae.

In other embodiments, the ventricular portion can comprise two or more discrete ventricular members that are each coupled to the atrial portion with an individual retention member, with the atrial portion including the prosthetic valve structure. In some embodiments, each of the ventricular members includes a plurality of hooks that are configured to engage the native mitral leaflets and/or annulus, and in some embodiments each of the ventricular members is coupled to the atrial portion by two or more retention members.

In some embodiments, at least one of the atrial portion and the ventricular portion includes one or more ratcheting mechanisms and the one or more retention members extend through the ratcheting mechanisms. The length of each retention member between the atrial portion and the ventricular portion can be shortened by pulling a free end of the retention member through the ratcheting mechanism or by advancing the ratcheting mechanism along the one retention member.

In some embodiments, the ventricular portion comprises two discrete ventricular members that each has a semi-annular shape, such that when the two ventricular members are joined together, they form a fully annular shape.

In some embodiments, the ventricular portion comprises four discrete ventricular members that are each coupled to the atrial portion with an individual retention member, and each of the four discrete ventricular members includes a hook or other feature for engaging the mitral leaflets and/or chordae.

In some embodiments, two discrete ventricular members each include a semi-annular portion that is placed under the mitral annulus, and each semi-annular portion is coupled to a detachable handle that projects generally perpendicularly from a semi-annular portion up through the mitral orifice and the left atrium. In some embodiments, the atrial portion includes an opening through which the two detachable handles can pass such that the atrial portion can be advanced over the two handles down toward the atrial side of the mitral annulus. The semi-annular portion of each ventricular member can include an outer arcuate body and an inner arcuate body that are joined at one end adjacent to the handle and that form a leaflet receiving gap between the inner and outer arcuate bodies, such that the semi-annular portion can be rotated by twisting the handle to trap a leaflet in the leaflet receiving gap.

In some embodiments, the retention members can be mounted to the atrial portion with a spring-biasing mechanism that urges the retention members atrially. The retention members can be actuated by a user (e.g., pressed toward the atrial body) to cause hooks on ventricular ends of the retention members to pass below the ventricular member(s), rotated to position the hooks under the ventricular member(s), then released to allow the hooks to engage the ventricular member(s) and draw the atrial and ventricular members together using a resilient spring force instead of manually applied tension.

The foregoing and other objects, features, and advantages of the disclosed technology will become more apparent from the following detailed description, which proceeds with reference to the accompanying figures.

BRIEF DESCRIPTION OF THE DRAWINGS

FIG. 3 shows an exemplary embodiment of the prosthetic mitral valve of FIG. 1, with the valve structure omitted for clarity.

FIG. 4 shows another exemplary prosthetic mitral valve including an atrial portion and a ventricular portion that are configured to be drawn together from opposite sides of the mitral valve with tensioning members. In this embodiment, the atrial portion includes the valve structure.

FIG. 7 shows another exemplary prosthetic mitral implant having an atrial member configured to include a prosthetic valve and two ventricular anchors that are configured to be drawn toward the atrial portion to anchor the device at the native mitral valve.

FIG. 8 shows an exemplary atrial member and two exemplary ventricular anchors similar to that shown in FIG. 7.

FIGS. 24 and 25 show an exemplary D-shaped ventricular member with a releasable handle.

FIG. 31 shows another exemplary device including an atrial body housing a prosthetic valve structure and an annular ventricular member, wherein the atrial body includes rotational retention members that engage with the ventricular member.

FIG. 32 is an atrial view of the device of FIG. 31.

FIG. 33 is a ventricular view of the device of FIG. 31.

FIG. 34 shows an enlarged view of one of the retention members of the device of FIG. 31.

FIG. 35 is a cross-sectional diagram showing the ventricular member of the device of FIG. 31 positioned under the native mitral valve annulus.

FIG. 36 is a cross-sectional diagram showing the device of FIG. 31 implanted at a native mitral valve, with a native mitral leaflet sandwiched between the atrial member, the ventricular member, and one of the retention members.

DETAILED DESCRIPTION

Disclosed herein are prosthetic devices and related methods that are configured to be implanted at the native mitral valve of the heart by clamping an atrial portion and a ventricular portion toward each other on opposite sides of the native mitral valve. The atrial and ventricular portions can be held in compression, clamping the native mitral valve and/or annulus between them. One or more tethers, tensioning members, or other retention members passing through the mitral valve orifice can couple the atrial and ventricular members together and keep them clamped onto the native mitral valve anatomy.

Figure 2:
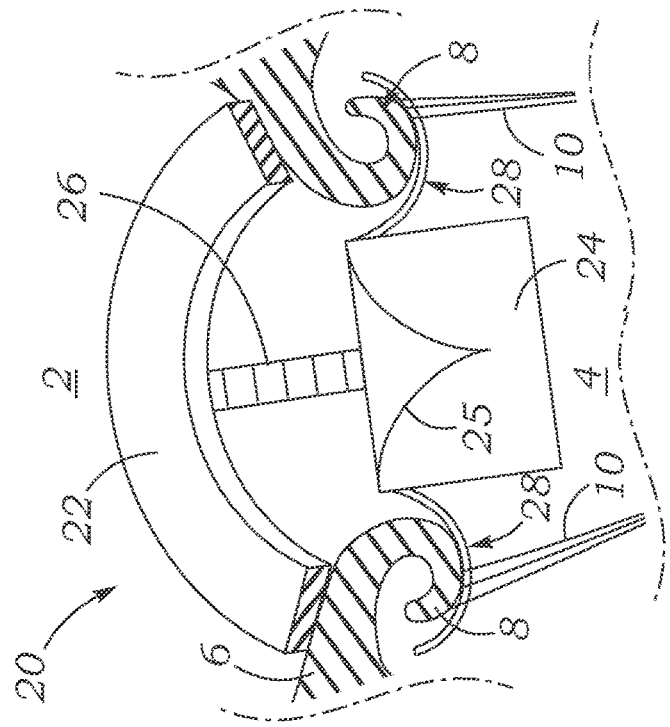
FIG. 2 is a cross-sectional view of the mitral valve showing the implanted prosthetic mitral valve of FIG. 1.
Figure 1:
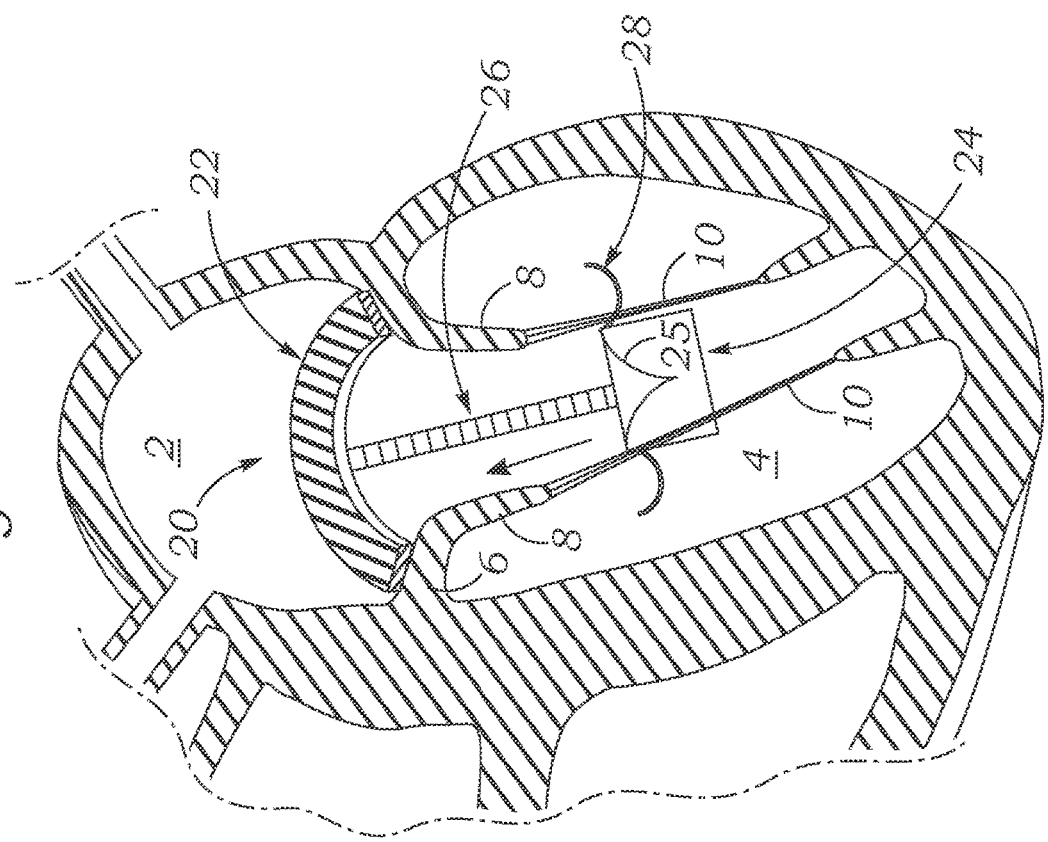
FIG. 1 is a cross-sectional view of the left side of the heart showing implantation of an prosthetic mitral valve assembly having an atrial portion and a ventricular portion that are drawn together from opposite sides of the mitral valve with tensioning members. The ventricular portion includes a valve structure in this embodiment.

FIGS. 1 and 2 illustrate an exemplary prosthetic mitral valve 20 being implanted at the native mitral valve. The prosthetic mitral valve 20 includes an atrial portion 22 that is positioned in the left atrium 2, a ventricular portion 24 that is positioned in the left ventricle 4, and one or more retention members 26 that extends between the atrial and ventricular portions. The ventricular portion 24 can include a prosthetic valve structure 25 (e.g., including one or more tissue leaflets) for replacing the functionality of the native mitral valve. As shown in FIG. 1, the ventricular portion 24 can be positioned in the left ventricle 4 below the native leaflets 8 with hooks 28 extending through the native chordae tendineae 10, while the atrial portion 22 is positioned in the left atrium 2 above the native mitral valve annulus 6. The atrial portion 22 can comprise a ring or annular structure, for example, that seats against the atrial surface of the annulus 6.

As shown in FIG. 2, the ventricular portion 24 can be moved upward toward the atrial portion 22 by shortening the length of the retention members 26 therebetween, such that the ventricular portion moves into the native valve orifice between the native leaflets 8 and the hooks 28 reach around the leaflets and pull the leaflets upward toward the annulus 6 and the atrial portion 22. As shown in FIG. 2, the leaflets 8 can be caused to fold back, curl up, and/or bunch-up due to pressure from the hooks 28, which causes the leaflets to pull on and tension the chordae 10. The ends of the hooks 28 may or may not contact the annulus 6 behind the leaflets 8. Compression of the leaflets 8 and/or annulus 6 between the atrial portion 22 and the hooks 28 can provide anchorage for the entire prosthetic mitral valve 20.

The retention members 26 can function in various alternative ways to help drawn and/or guide the atrial and ventricular portions 22, 24 toward each other and to keep them clamped to the native mitral anatomy. In some embodiments, the retention members 26 can comprise one or more elongated strips that include notches, ridges, or similar features spaced at intervals along their lengths. One end of each retention member 26 can be fixed to one of the atrial or ventricular members 22, 24, while the other end of each retention member can pass through a respective ratcheting mechanism on the other of the atrial or ventricular members. The retention members 26 can then be moved through the ratcheting mechanisms to allow the atrial and ventricular members 22, 24 to move toward each other. This type of retention member 26 can function similar to a "zip tie" or a "cable tie" in that the retention member 26 can move in one direction through the ratcheting mechanism to tighten the prosthetic mitral valve 20, but is prevented from moving in the opposite direction through the ratcheting mechanism by the notches or ridges on along the strip. In other embodiments, a retention member strip may not have any notches or ridges or similar features, and instead have a smooth surface that slides through a locking mechanism or other receiving aperture such that an infinite degree of tightening can be achieved. In such embodiments, when the desired degree of tension has been achieved, a clip or other retention device can be applied to each strip just beyond the aperture in the atrial or ventricular body through which the strip passes to prevent the strip from sliding back out and loosening. Other exemplary techniques for securing the retention members at a desired tension can include welding, bonding, knotting, or using a locking member, for example, a pin or clip. Because of the various alternative ways in which the retention members can be secured to maintain a desired tension between the atrial and ventricular portions, any description of a ratcheting mechanism herein should be considered to also support any equivalent alternative tightening and securement techniques, such as is described in this paragraph. In some embodiments, an excess portion of a retention member, for example, a portion that has passed through the ratcheting mechanism, is removed after tensioning, for example, by cutting, shearing, and/or breaking off.

FIG. 3 shows an exemplary prototype of the prosthetic mitral valve 20 (the valve structure 25 is omitted for clarity) including two ratcheting-type retention members 26. In the embodiment of FIG. 3, the retention members 26 includes strips that are fixed to the atrial portion 22 and that pass through corresponding ratcheting mechanisms 27 at the ventricular portion 24. In other embodiments, a different number of retention strips and ratcheting mechanisms can be included, and the locations, lengths, and spacings can also vary.

With the embodiment shown in FIG. 3, from the position shown in FIG. 1, the ventricular ends of the retention strips 26 can be held stationary and/or tensioned (with the atrial portion 22 providing resistance against the annulus 6) while the ventricular portion 24 and the ratcheting mechanisms 27 are moved upward over the strips toward the atrial portion 22.

In an alternative embodiment (not shown) that is similar to the embodiment shown in FIG. 3, the ratcheting mechanisms 27 can be included in the atrial portion 22 instead of the ventricular portion 24. In such an embodiment, the atrial portion 22 can be held stationary against the mitral annulus 6 while the atrial ends of the strips are pulled upward through the ratcheting mechanism 27 drawing the ventricular portion 24 upward toward the atrial portion 22. Other embodiments include ratcheting mechanisms on both the atrial and ventricular portions, for example, including retention members that are not fixed to either the atrial or ventricular portions, or including a first retention member fixed to the atrial portion and a second fixed to the ventricular portion. Such alternative configurations also apply to all of the embodiments of the prosthetics disclosed herein.

In other embodiments, the retention members can comprise a resiliently deformable (e.g., an elastomeric, elastic, and/or spring-like) material that is stretched to the position shown in FIG. 1 and then allowed to resiliently shorten to the configuration shown in FIG. 2 to clamp the atrial and ventricular portions 22, 24 onto the native mitral anatomy. Similarly, in any of the other embodiments described herein, elastomeric, elastic, or spring-like tethers can be used instead of or in addition to the described ratcheting mechanisms or other described retention systems in order to draw the atrial and ventricular bodies toward each other and to maintain a desired tension after implantation.

The prosthetic mitral valve 20 and similar alternative embodiments can be delivered and implanted by transcatheter techniques, such as via transfemoral, transaortic, transseptal, transventricular, or transatrial delivery. In such embodiments, the prosthetic mitral valve can be radially compressed and loaded into a catheter for delivery, then expanded (via a balloon, self-expansion, or otherwise) at the native valve site. For example, in a transventricular delivery through the wall of the left ventricle, a delivery catheter can release and/or cause the atrial portion 22 to expand in the left atrium and release and/or cause the ventricular portion 24 to expand in the left ventricle, such as via resilient self-expansion, with the retention members 26 extending through the mitral valve orifice. After expansion, the atrial 22 and ventricular 24 portions can be drawn together using the retention members to anchor around the native mitral valve. Any of the devices disclosed herein can also be surgically implanted.

FIG. 4 illustrates another exemplary prosthetic mitral valve 40. The prosthetic mitral valve 40 includes an atrial portion 42 positioned on the atrial side of the mitral valve, ventricular members 48 that are positioned in the left ventricle, and retention members 48 that span between the atrial portion 42 and the ventricular members 46. In the illustrated embodiment, the atrial portion includes a valve structure 44. During implantation, the atrial portion 42 is positioned with the valve structure 44 extending downwardly through the mitral orifice with a peripheral rim of the atrial portion overlying and optionally sealing against the mitral annulus. The ventricular members 46 are positioned in the left ventricle below the native leaflets and include hooks or fingers that extend through the native chordae tendineae. The retention members 48 can be fixed at their lower ends to the ventricular members 46 and coupled to the atrial portion. In some embodiments, the atrial portion 42 can include a ratcheting mechanism coupled to each retention member 48 such that each retention members can be pulled up through the corresponding ratcheting mechanism to draw each ventricular member 46 upward toward the atrial portion 42, causing the hooks of the ventricular members to engage the native mitral leaflets and/or chordae tendineae in a similar fashion as shown and described with respect to FIG. 2.

Figure 5C:
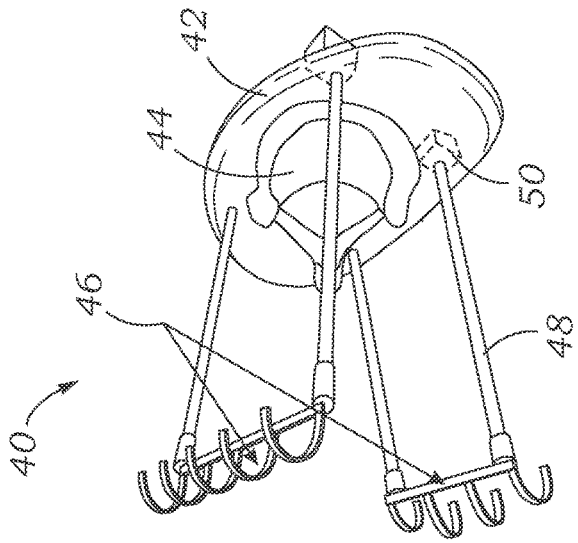
FIGS. 5A-5C show an exemplary embodiment of the prosthetic mitral valve similar to that shown in FIG. 4.
Figure 5B:
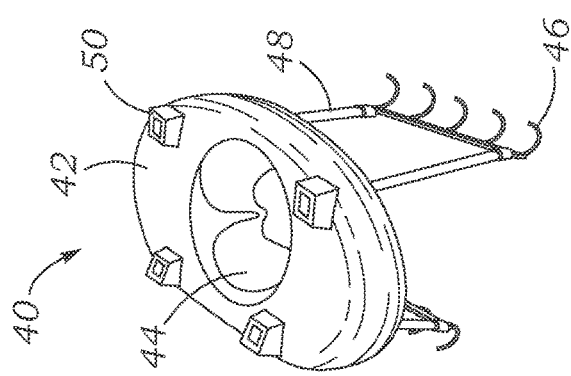
Figure 5A:
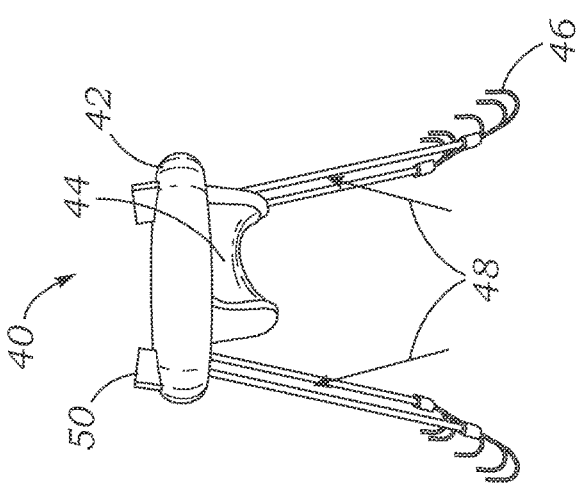

FIGS. 5A-5C show an exemplary prototype of the prosthetic mitral valve 40. The prototype includes two ventricular members 46, each coupled to the atrial portion 42 by two retention members 48 that pass through respective ratcheting mechanisms 50 located on the atrial portion 42 adjacent to the valve structure 44. In this prototype, a first ventricular member 46 includes four hooks and a second ventricular member includes five hooks, reflecting the asymmetric geometry of the mitral valve.

Figure 6C:
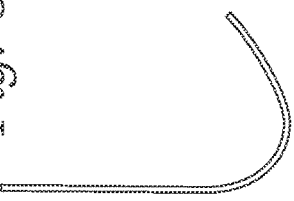
FIGS. 6A-6C show exemplary configurations of ventricular anchors.
Figure 6B:
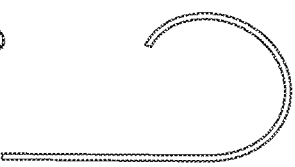
Figure 6A:
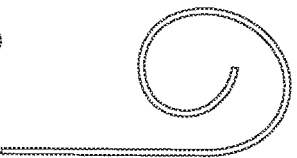

FIGS. 6A-6C show various optional configurations of the hooks 46. In FIG. 6A, the hook curls through more than about 360° such that the free end is not exposed. In FIG. 6B, the hook curls through more than about 180°, In FIG. 6C, the hook is curled between about 90° and about 180°. In some embodiments, the hooks can comprise nitinol or other superelastic material that allows the hooks to be straightened out during delivery and allowed to re-curl back to the positions shown in FIGS. 6A-6C or to other operative positions for engaging the leaflets, chordae tendineae, and/or mitral valve annulus.

FIGS. 7 and 8 show another exemplary prosthetic mitral valve 60 that includes two arcuate ventricular members 64, each coupled to the atrial portion 62 by two retention members 66 (FIG. 7) that extend from locations 76 (FIG. 8) on the ventricular members and that pass through ratcheting mechanisms 70 (FIG. 8) located on the atrial portion 62 adjacent to a central region 72. A valve structure is located at the central region, but is omitted for clarity in FIGS. 7 and 8. In this prototype, the ventricular members 64 each comprise an about 180° arcuate shape and includes a plurality of hooks 68 disposed around the radially outer edge of the arcuate shape. The two ventricular members 64 can abut each other when implanted to form a fully annular shape that corresponds to the annular outer sealing rim 74 of the atrial portion 62. The shape of the sealing rim 74 can be a D-shape, an oval, or a kidney shape that corresponds generally to the shape of the native mitral valve. When the ventricular members 64 are pulled upward toward the atrial portion 62, the hooks 68 extend behind the leaflets, clamping the native valve structure between the atrial portion and the two ventricular members.

Figure 9:
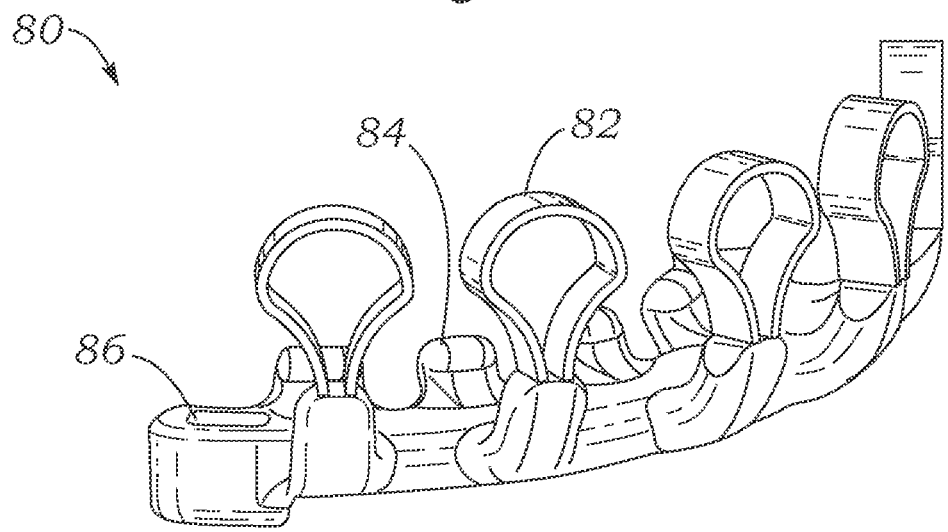
FIGS. 9-12 show an exemplary ventricular anchor having flexible engagement members, such as for placement in the native anatomy and/or reduction of paravalvular leakage.
Figure 10:
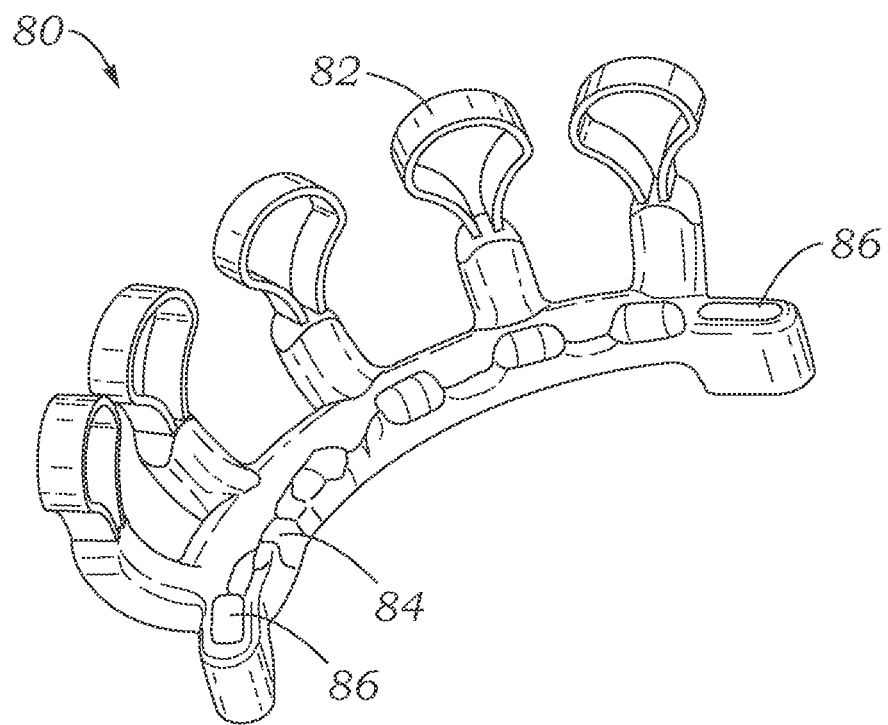

FIGS. 9 and 10 show an alternative ventricular member 80 that includes flexible engagement members 82 instead of hooks disposed along the radial outer edge of the arcuate shape. Each of the flexible engagement members 82 can comprise a loop of flexible material that provides a curved upper surface for engaging the mitral valve tissue on the underside of the mitral valve annulus. The curved, flexible upper surface of the engagement members 82 can provide a more uniform pressure distribution that is less traumatic to the tissue relative to embodiments that include individual hooks that are more rigid than the flexible engagement members. It can also allow for a lower profile member that can more readily fit through the chordae of the native anatomy. The radially inner edge of the ventricular members 80 can include additional projections 84 that help to contain the leaflets. The ventricular members 80 can also include features 86 at each end for attachment of the lower ends of retention members that couple the ventricular members to an atrial portion.

Figure 11:
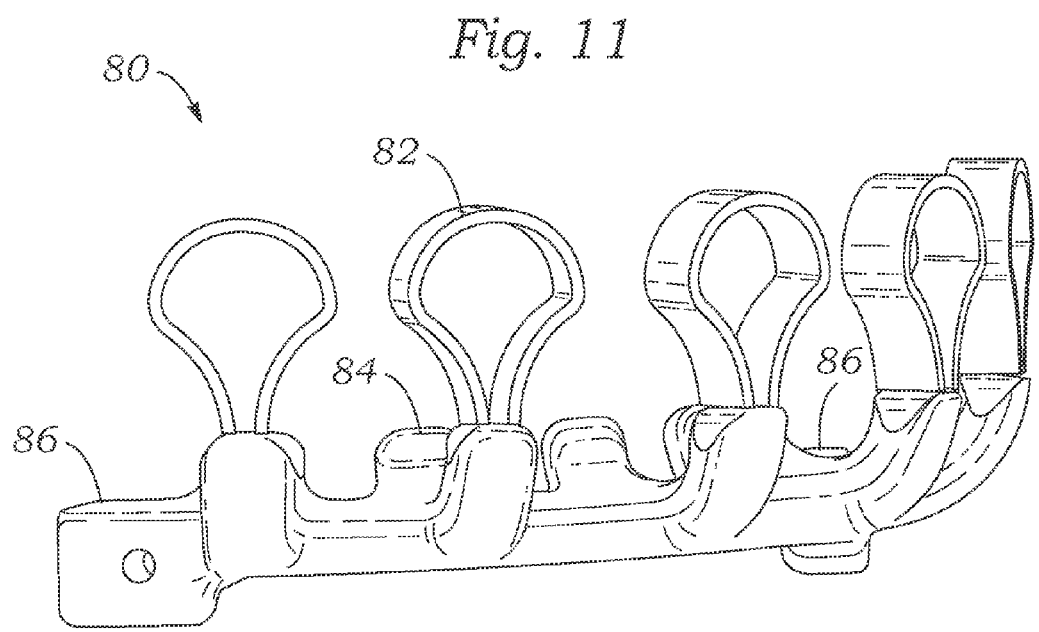
Figure 12:
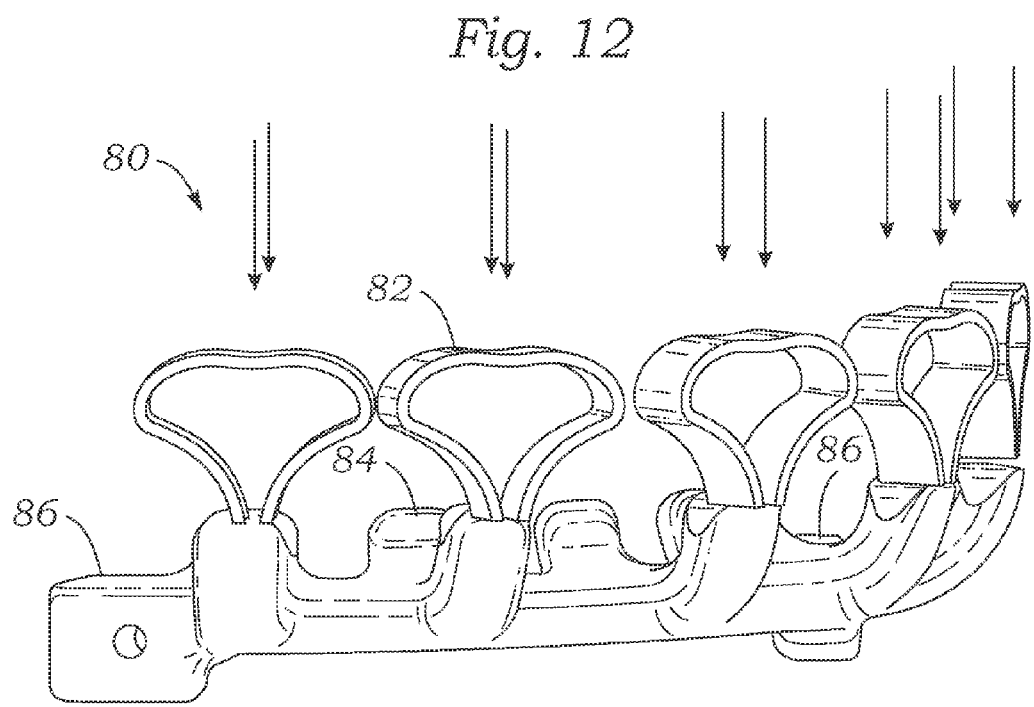

FIG. 11 shows the engagement members 82 in their unconstrained states, and FIG. 12 illustrates the deformation of the engagement members 82 when a downward force is applied thereto, such when contacting the lower surface of the mitral valve annulus. In FIG. 12, the upper surfaces are flattened, providing a more uniform pressure distribution along the length of the arcuate curve of the ventricular member 80.

Figure 13:
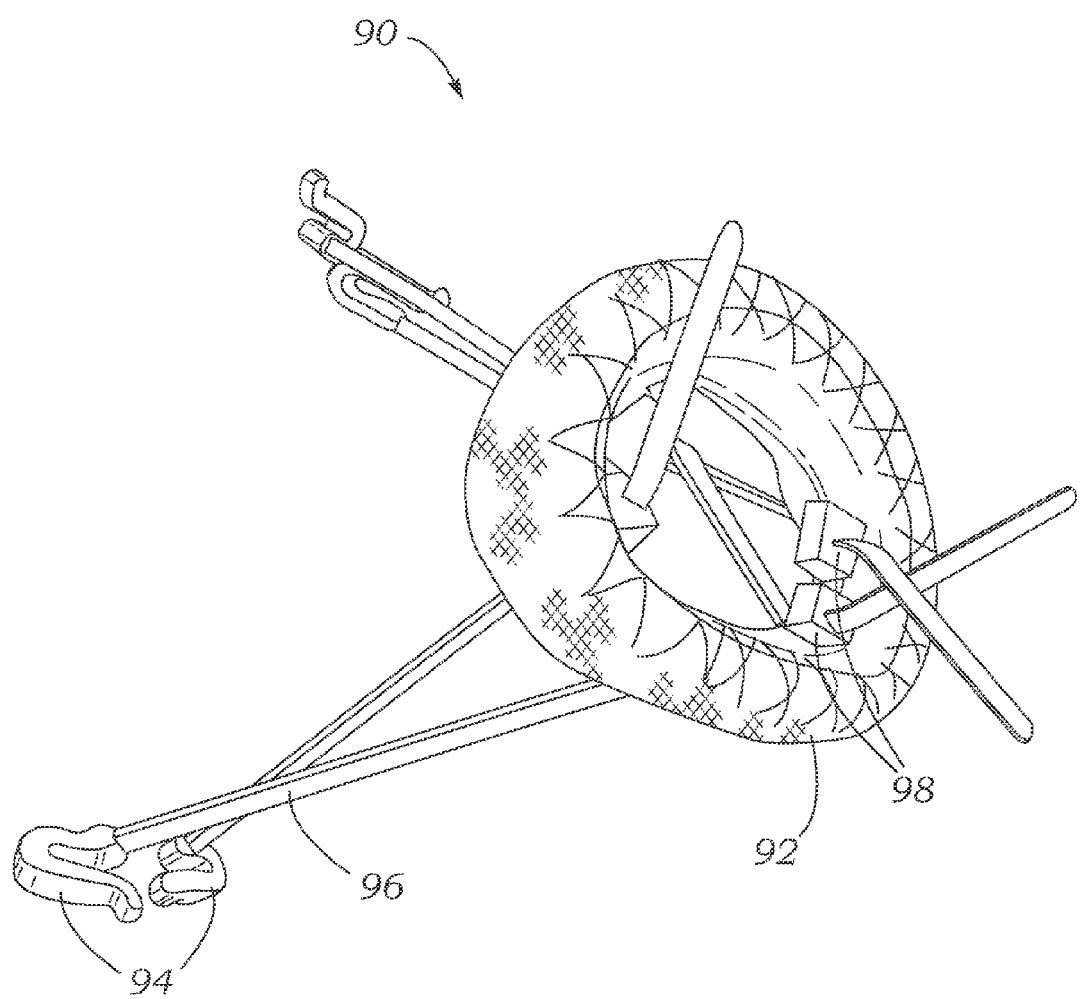
FIG. 13 shows another exemplary prosthetic mitral implant having an atrial member configured to include a prosthetic valve and four ventricular anchors that are configured to be drawn toward the atrial portion to anchor the device at the native mitral valve.
Figure 14:
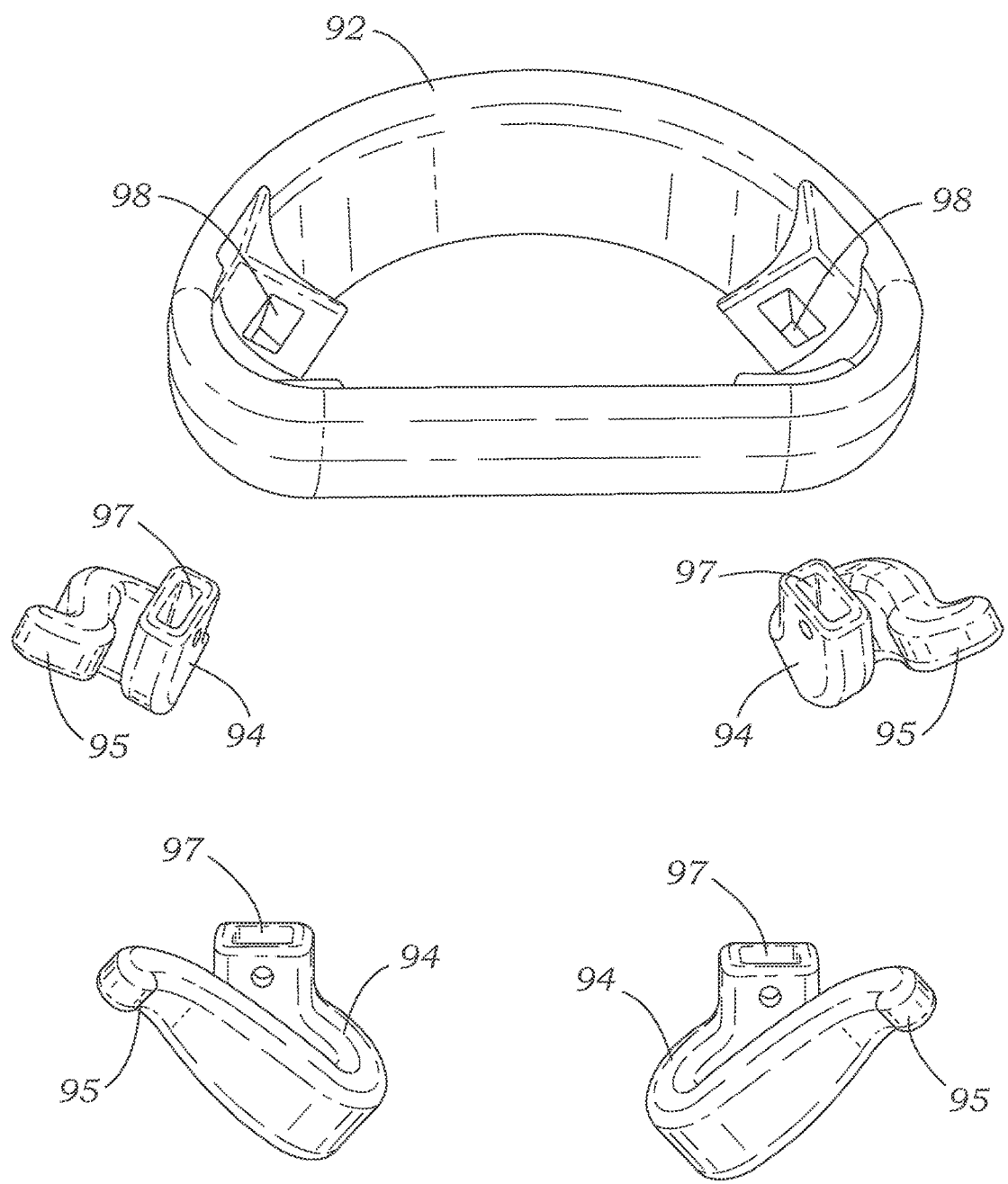
FIG. 14 shows another embodiment including an exemplary atrial member and four exemplary ventricular anchors similar to the embodiment shown in FIG. 13.
Figure 15:
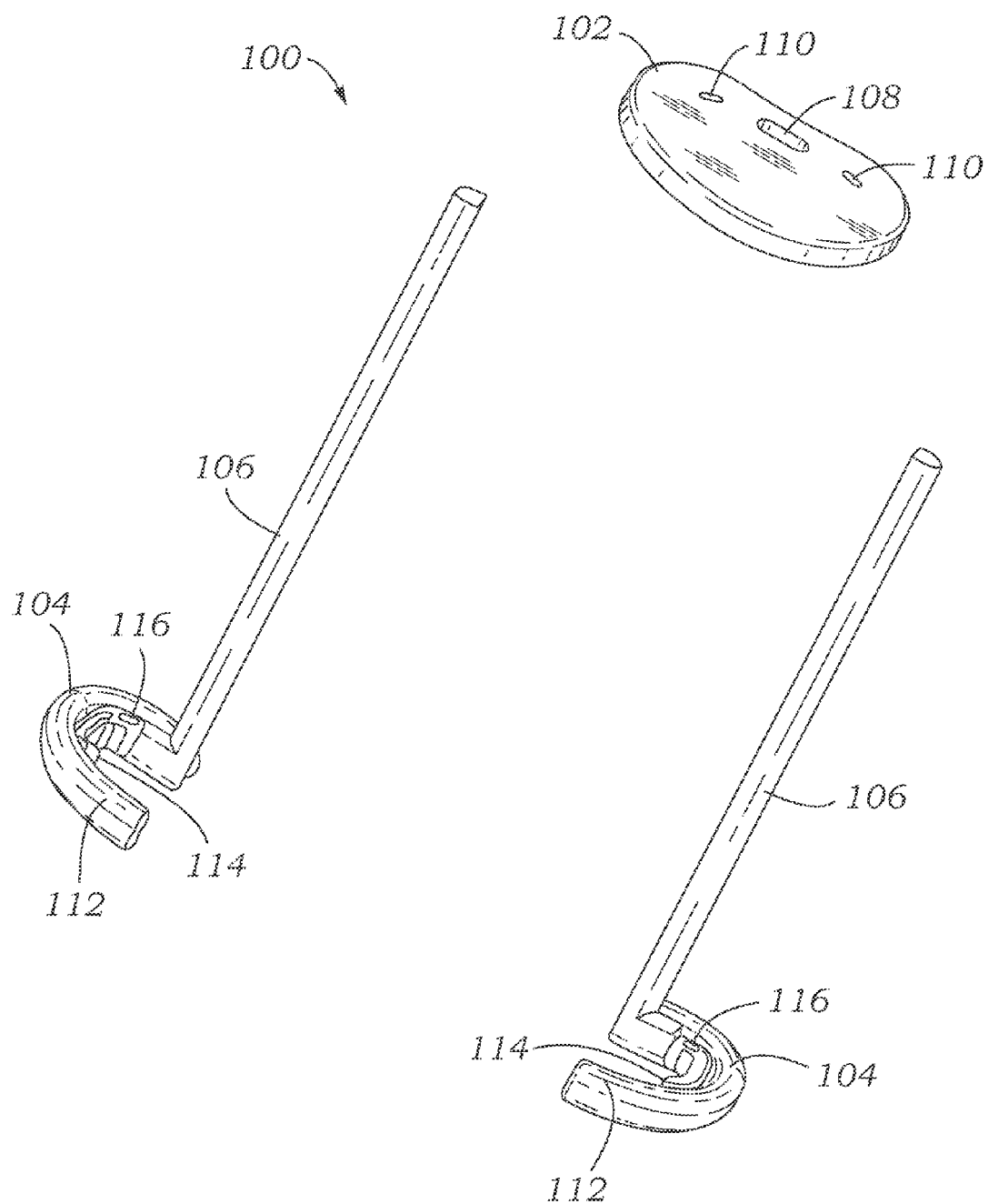
FIGS. 15-17 shows another exemplary prosthetic mitral implant including an atrial member configured to include a prosthetic valve and two ventricular members that are configured to be drawn toward the atrial portion to anchor the device at the native mitral valve. The ventricular members include C-shaped anchors and detachable handles that are configured to extend through an opening in the atrial member.

FIGS. 13 and 14 show another exemplary prosthetic mitral valve 90 that includes an atrial portion 92, four ventricular members 94, and four retention members 96 coupling the ventricular members to the atrial portion. The atrial portion includes an outer rim configured to seat against the upper side of the native mitral annulus and an inner region where a valve structure (not shown) is disposed such that the valve structure projects downwards into the mitral valve orifice. Each of the ventricular members 94 can include a hook 95 that engages the native mitral leaflets, chordae, and/or mitral valve annulus, and a feature 97 that attaches to the lower end of one of the retention members 96. The upper end of each retention member 96 extends through a corresponding ratcheting mechanism 98 in the atrial portion 92 such that the ventricular members 94 can be pulled up towards the atrial portion by pulling the upper ends of the retention members through the ratcheting mechanisms. The ratcheting mechanisms 98 can be located near the commissure regions of the mitral valve where the anterior and posterior leaflets join. As shown in FIG. 13, two of the ratcheting mechanisms 98 are disposed at a first location of the atrial portion 92 that is configured to be placed over one of the native commissures, and the other two ratcheting mechanisms are disposed at a location on the other side of the atrial portion that is configured to be placed over the other native commissure.

The two hooks 95 coupled to the two ratcheting mechanisms 98 that are closer to the anterior mitral leaflet can be engaged to the A2 portion of the anterior leaflet between the chordae tendineae. Similarly, the two hooks 95 coupled to the two ratcheting mechanisms 98 that are closer to the posterior mitral leaflet can be engaged to the P2 portion of the posterior leaflet between the chordae tendineae. During implantation, the retention members 96 can be initially oriented at an angle from the longitudinal axis of the native mitral valve (e.g., the direction extending between the left atrium and the left ventricle through the mitral valve) because the hook 95 is located closer to the middle of the leaflet (e.g., the A2 or P2 region), while the ratcheting mechanism 92 is located closer to the commissure. As the retention members 96 are pulled up through the atrial portion 92, the ventricular members 94 are pulled upward toward the atrial portion, and also outwardly toward the commissures. In addition, the hooks 95 can be configured to extend both upwardly and outwardly in a similar manner (see FIG. 14). In the fully implanted configuration, the ventricular members 94 are drawn up around the leaflets with the leaflets bunching up and/or curling up, and with the hooks 95 extending around behind the leaflets at the juncture where the chordae tendineae attach to the leaflet. The angled tension on the ventricular members 94 can pull the chordae tendineae laterally toward the commissures.

Figure 16:
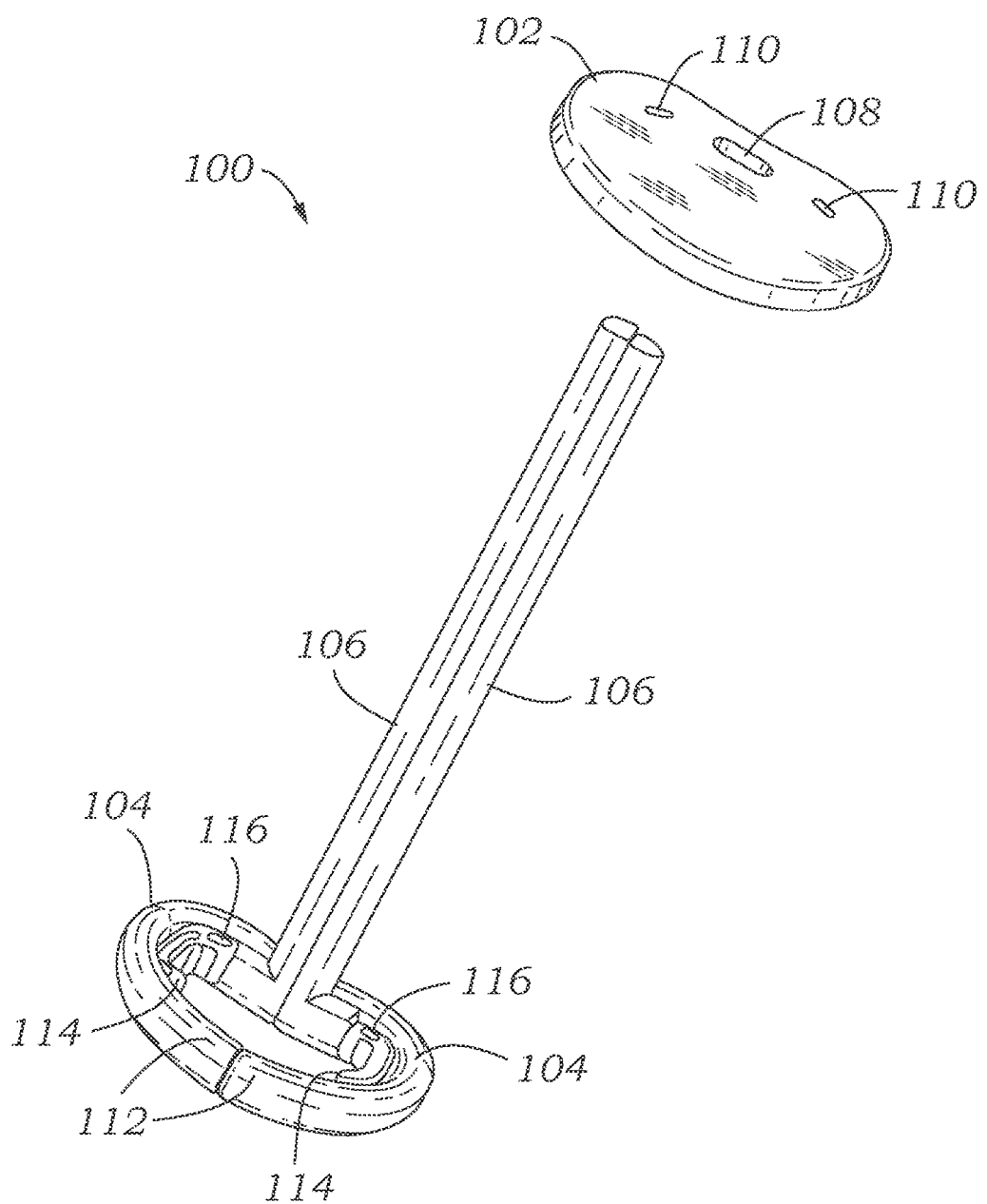
Figure 17:
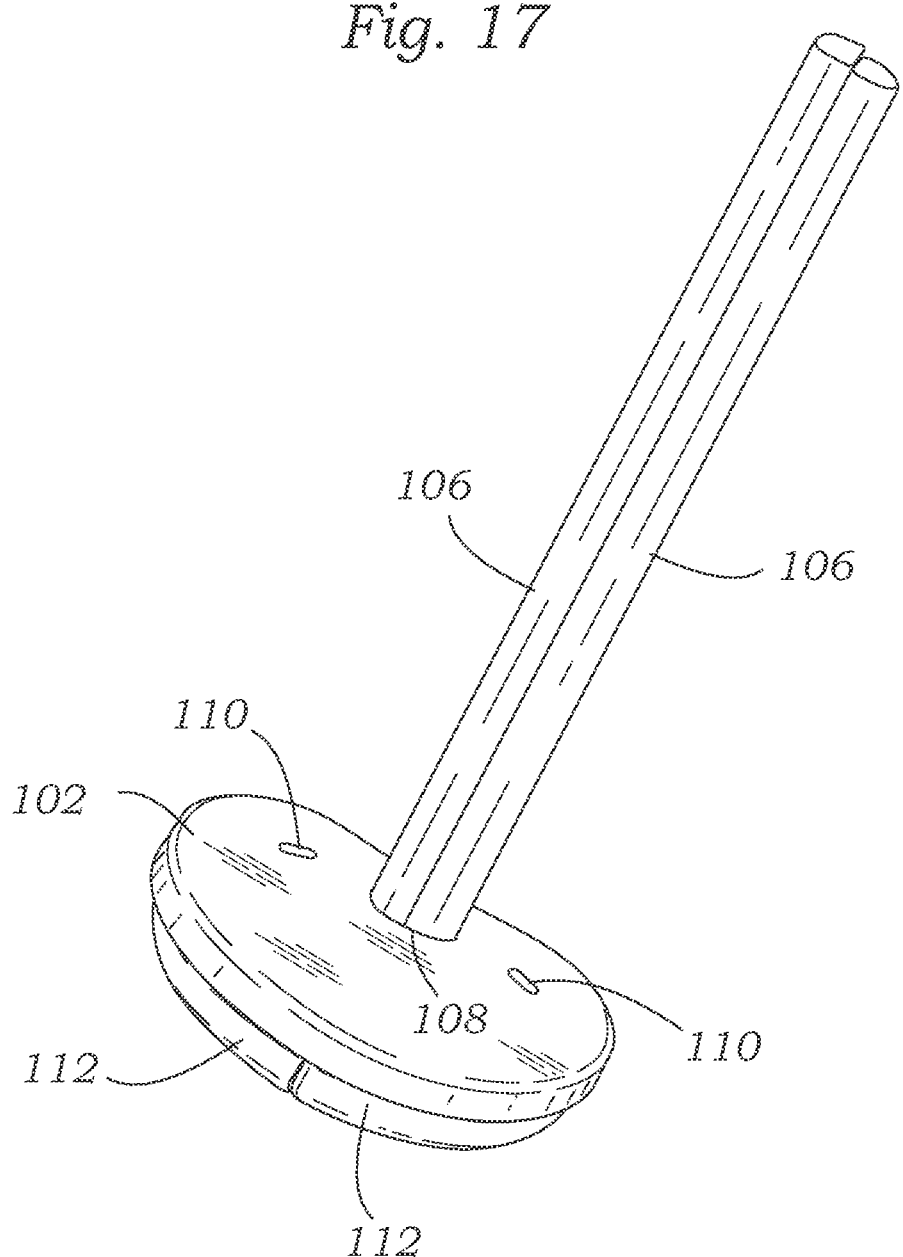
Figure 18:
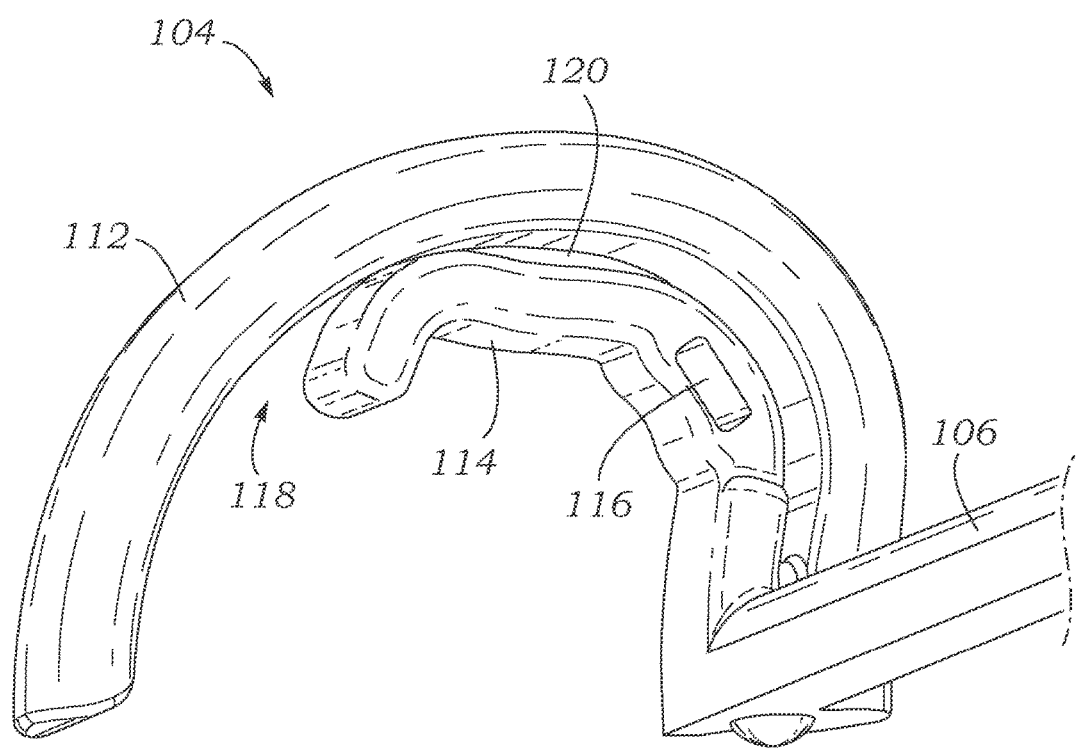
FIG. 18 is a detailed view of the C-shaped anchors of FIGS. 15-17. Each anchor includes an outer arcuate member and an inner arcuate member with a leaflet receiving space therebetween.

FIGS. 15-19 illustrate another exemplary prosthetic heart valve 100 that includes an atrial portion 102 and ventricular members 104 that are placed on opposite sides of the native mitral valve and drawn toward each other during implantation. The atrial portion 102 is configured to seat on top of the native mitral annulus and includes a valve structure (not shown) located at its central region that projects downwards into the mitral orifice. The two ventricular members 104 each have a generally C-shaped lower portion including an arcuate outer body 112 and a smaller arcuate inner body 114 (FIG. 18). The inner and outer bodies 112, 114 are coupled to each other at a first end of the inner body 114 while forming a gap 118 at a second end of the inner body. The gap 118 connects with an open space 120 between the inner and outer bodies. A detachable handle 106 extends upwardly at a generally right angle from the lower C-shaped portion at or about where the first end of the inner body 112 connects to the outer body 114. The inner body 114 can also include a feature 116 for attaching to a retention member (not shown).

As shown in FIG. 16, when the two ventricular members 104 are brought laterally together, the lower C-shaped portions form a generally D-shaped annular ring that is similar in shape to the atrial portion 102 and the shape of the native mitral valve. During implantation, the ventricular members 104 can be implanted one-at-a-time in engagement with the native mitral leaflets, then the atrial portion 102 can be lowered over the two adjacent handles 106 with the handles passing through an opening 108 in the atrial portion, as shown in FIG. 17.

A first ventricular member 104 can be initially placed in the left ventricle with the handle 106 projecting up through the mitral valve and the left atrium, and with the lower C-shaped portion adjacent to one of the native mitral leaflets. In an exemplary procedure, the free end of the outer arcuate body 112 (the end opposite the handle 106) can be directed (e.g., rotated) behind the anterior leaflet (e.g., at the A2 region) and toward one of the commissure regions, capturing the anterior leaflet and/or the chordae tendineae in the gap 118 (see FIG. 18) with the inner body 114 remaining on the inside of the anterior leaflet and chordae. Referring to the view shown in FIG. 18, the handle 106 can be used to rotate the ventricular member 104 in a counter-clockwise direction to capture the anterior leaflet in the gap 118. Further counter-clockwise rotation advances the outer body 112 past the commissure region and behind the posterior leaflet toward the P2 region while the anterior leaflet moves through the gap 118 into the open space 120 and toward the juncture of the inner and outer bodies 112, 114 near the base of the handle 106. At this point, the outer body 112 is positioned behind the leaflets under one half of the mitral annulus and the inner body 114 is positioned along the inner side of the leaflets, with lateral portions of both leaflets (e.g., the A1 and P1 regions, or the A3 and P3 regions) and/or portions of the chordae captured between the inner and outer bodies.

With the first ventricular member 104 positioned as described in the preceding paragraph, the second ventricular member, which is about a mirror image of the first ventricular member in the illustrated embodiment, can be implanted in the same way at the opposite side of the mitral valve using a minor-image procedure. Once the second ventricular member 104 implanted, the free ends of the outer bodies 112 can touch each other or be near each other, behind the P2 region of the posterior leaflet, while the bases of the two handles 106 can be touching or adjacent at the A2 region of the anterior leaflet. The two outer bodies 112 tether can form an annular D-shaped body that extends around behind the leaflets under the mitral annulus. As shown in FIG. 17, the atrial portion 102 can then be lowered over the handles 106 onto the upper surface of the mitral annulus with the valve structure (not shown) extending down between the inner bodies 114. Retention members (not shown), such as those described and illustrated herein for the embodiments 20, 40, 60, 80, and 90 can extend from the features 116 of the inner bodies 114 can pass through respective ratcheting mechanisms 110 in the atrial body 102. The atrial body 102 and the outer bodies 112 of the ventricular members 104 can be clamped onto the native mitral annulus by tightening the retention members. The handles 106 can then be detached and removed.

Figure 19:
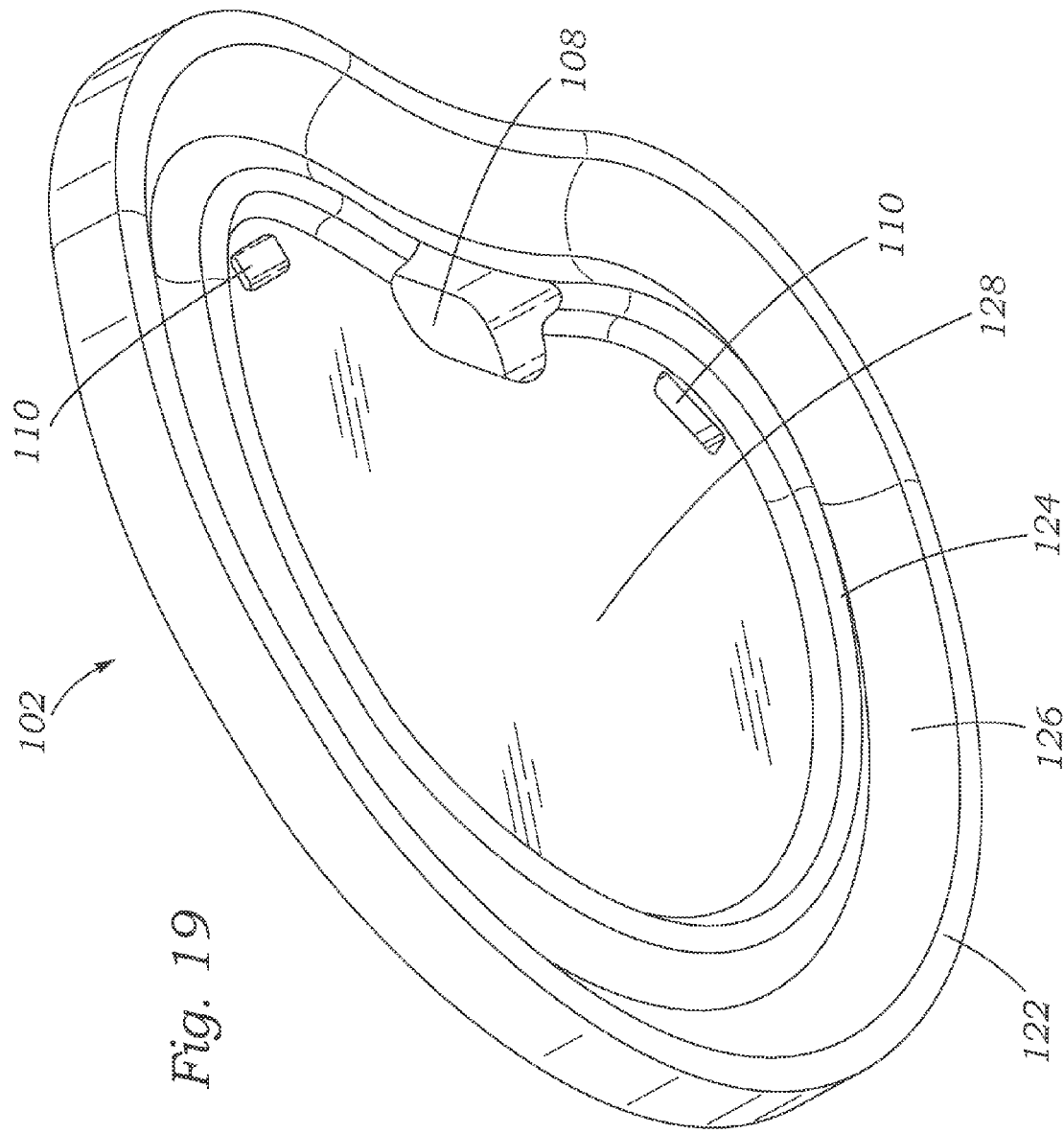
FIG. 19 shows a ventricular side of the atrial member of FIGS. 15-17.

FIG. 19 shows an embodiment of a lower surface of the atrial portion 102 with the valve structure not shown in the central region 128. The lower surface of the atrial portion 102 can include an outer rim 122 and an inner rim 124 that form a trough 126 between them. The rounded upper surfaces of the two outer bodies 112 of the ventricular members 104 can urge or press the mitral annulus and/or the bases of the mitral leaflets upward into the trough 126 to provide greater engagement, to distribute stress, and to provide a more accurate registration between the ventricular members and the atrial portion.

In some embodiments, the handles 106 can be disconnected from the rest of the ventricular members 104 after implantation, or all or a portion of the handles 106 can be cut off or otherwise removed after implantation.

Figure 20:
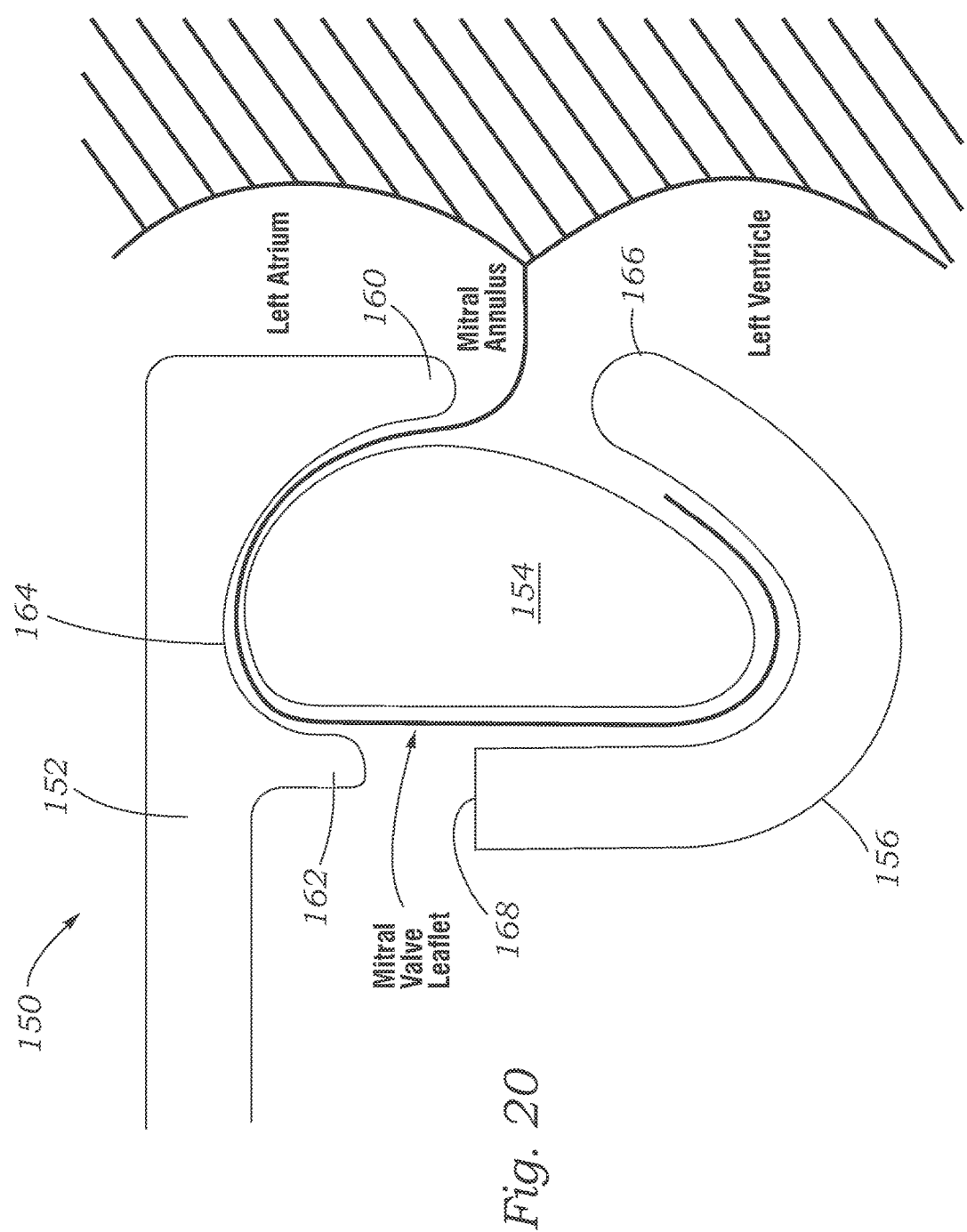
FIG. 20 is a cross-sectional view of another exemplary prosthetic implant secured at the mitral valve region. The mitral valve leaflet is curled around a ventricular sealing member and sandwiched between a ventricular retention member below and an atrial sealing member above.

FIG. 20 is a cross-sectional view of one side of another exemplary prosthetic mitral valve 150 engaging a native mitral valve leaflet. The prosthetic mitral valve 150 can include an atrial portion 152 with a valve structure, similar to the atrial portion 102. The atrial portion 152 can also include an outer rim 160, and inner rim 162, and a trough 164 between the outer and inner rims, which is similar to the embodiment of the atrial portion 102 illustrated in FIG. 19. The prosthetic mitral valve 150 can also include a ventricular sealing member 154 that has an upper surface with a profile complementary to the profile of the trough 164 and dimensioned to register therewith, to capture the mitral annulus and/or base portions of the mitral leaflets therebetween. The ventricular sealing member 154 can comprise a generally annular ring, such as a generally D-shaped ring, or a partially annular body, or a plurality of bodies (for example, similar to the outer bodies 112) that combine to form a fully or partially annular ring that extends around behind the leaflets. One or more ventricular retention members 156 can be used to compress the ventricular sealing member 154 and the atrial portion 152 together, clamping the native annulus and/or leaflets therebetween. The retention member 156 can include hooked ends 166 that extend around the lower surface of the sealing member 154 and that can capture the free ends of the leaflets therebetween, as shown in FIG. 20. The retention member 156 can also include one or more features 168 that attach to or include tension members or strips (not shown) that extend up through the mitral orifice and through ratcheting mechanisms (not shown) in the atrial portion, which can be tightened or tensioned to draw the atrial portion 152, the ventricular sealing member 154, and the ventricular retention member 156 together.

Figure 21A:
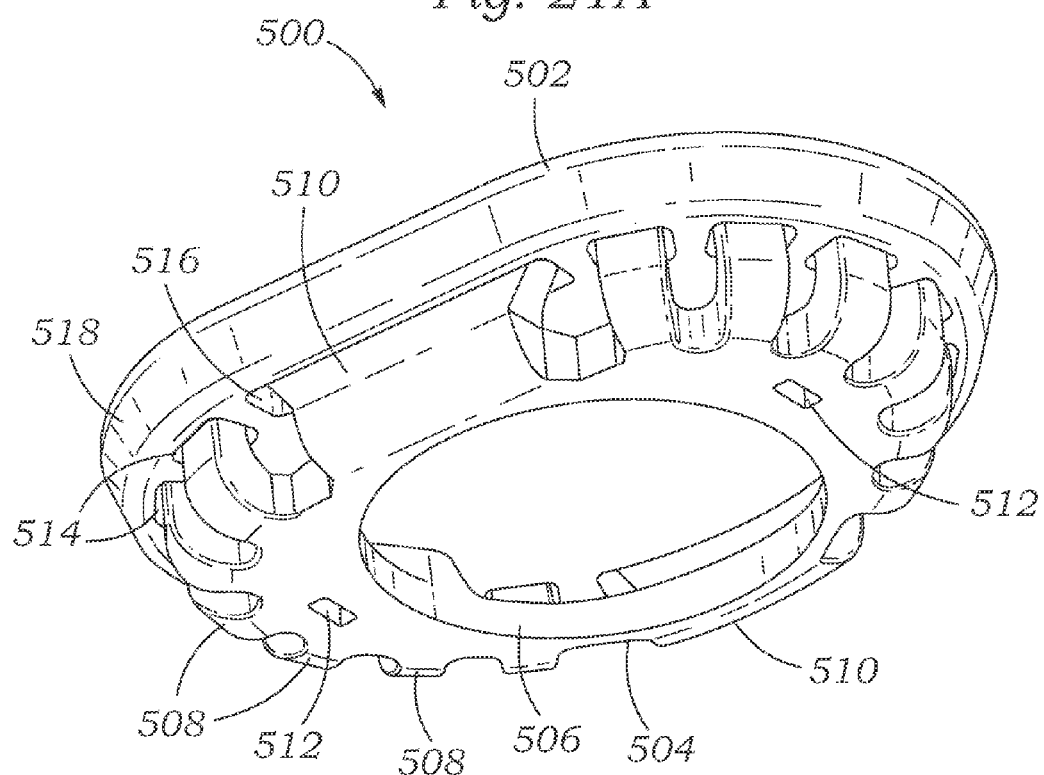
FIG. 21A shows another exemplary device including an atrial body and a one-piece ventricular body that are retained together such that claws of the ventricular body are positioned with recesses of the atrial body.
Figure 21B:
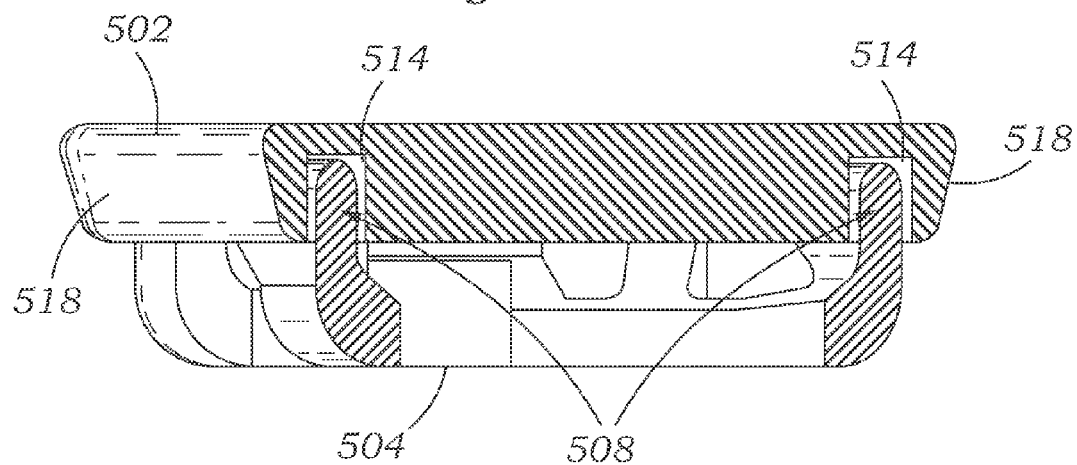
FIG. 21B is a cross-sectional view of the device of FIG. 31, showing the positioning of the claws in the recesses.

FIGS. 21A and 21B illustrate another exemplary device 500 that is configured to be implanted at the native mitral valve of the heart by clamping tissue of a native mitral valve between an atrial portion 502 and a ventricular portion 504. The atrial and ventricular portions 502, 504 can be held in compression using retention members (not shown), clamping the native mitral valve between them. The retention members can comprise the ratcheting-type or other tensionable devices described herein. The retention members engage with features 512 in the ventricular portion 504 and corresponding features in the atrial portion 502 that are not shown.

The ventricular member 504 can comprise a single, fully annular body with a central opening 506 and a plurality of claws 508, 510 disposed about the perimeter. In the illustrated example, one or more of the claws 510 can be larger and/or broader that other claws 508. Each of the claws 508, 510 curves and/or extends in the atrial direction. The atrial portion 502 can comprise corresponding recesses 514, 516 that are arranged and configured to receive the free ends of the claws 508, 510. The atrial portion 502 can also include a central prosthetic valve structure (not shown) mounted between the recesses 514, 516.

As the atrial and ventricular portions 502, 504 are drawn together from opposite sides of the native mitral valve, the claws 508, 510 engage the native annulus and/or leaflets, pushing the tissue into the recesses 514, 516. For example, FIG. 21B is a cross-sectional view showing the free ends of the claws 508 positioned within the recesses 514, forcing the native valve tissue to assume a tortuous path around the tips of the claws 508, 510 within the recesses 514, 516, which improves sealing and reduces paravalvular leakage. The registration between the claws 508, 510 and the recesses 514, 516 can also help guide the atrial and ventricular portions together in proper alignment.

Figure 22:
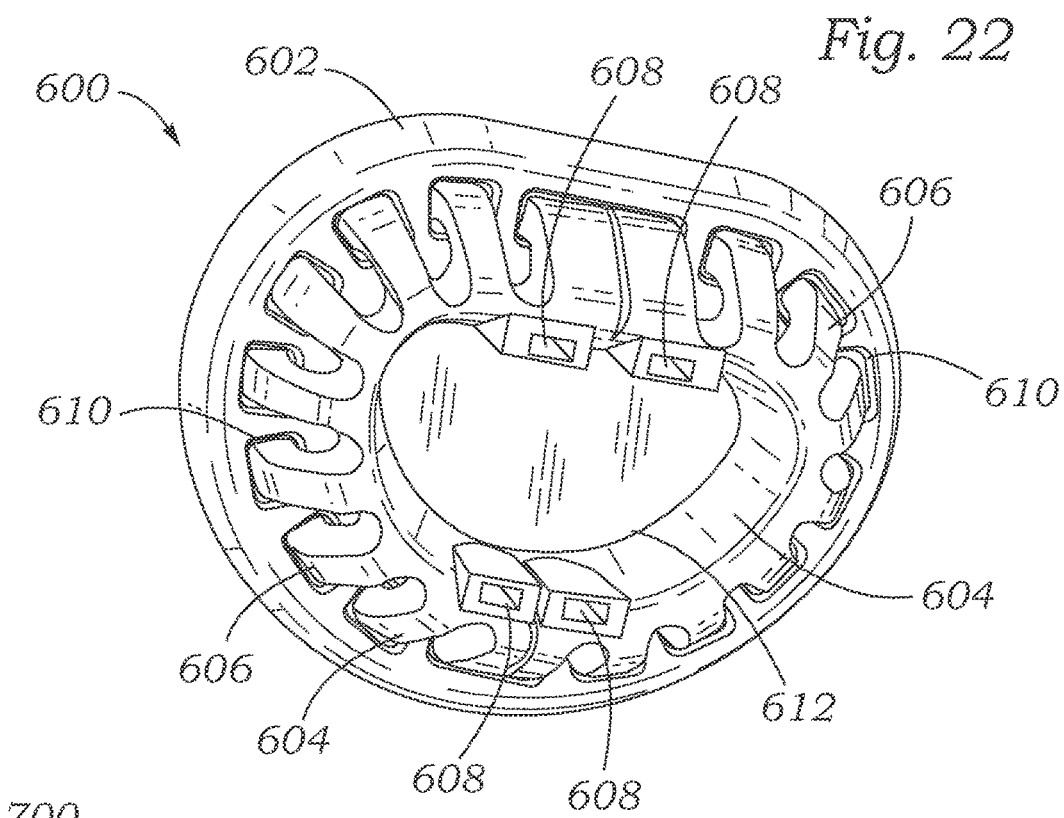
FIG. 22 shows another exemplary device including an atrial body and a two-piece ventricular body that are retained together such that claws of the ventricular body are positioned with recesses of the atrial body.

FIG. 22 shows another device 600 that is that is similar to device 500, except that the ventricular portion 604 comprises two half-annular bodies instead of the single-piece, fully-annular body 504. The ventricular members 604 can join together to form a central opening 612 with the plurality of claws 606 disposed about the perimeter. The atrial portion 602 comprises corresponding recesses 610 that are arranged and configured to receive the free ends of the claws 606. The atrial portion 602 can also include a central prosthetic valve structure (not shown) mounted between the recesses 610. The retention members attach to the ventricular portions 604 at features 608 and attach to the atrial portion 602 at corresponding features (not shown).

As the atrial and ventricular portions 602, 604 are drawn together from opposite sides of the native mitral valve, the claws 606 engage the native annulus and/or leaflets and push the tissue into the recesses 610, forcing the native valve tissue to assume a tortuous path around the tips of the claws 606 within the recesses 610, which improves sealing and reduces paravalvular leakage. The registration between the claws 606 and the recesses 610 can also help guide the atrial and ventricular portions together in proper alignment.

Figure 23:
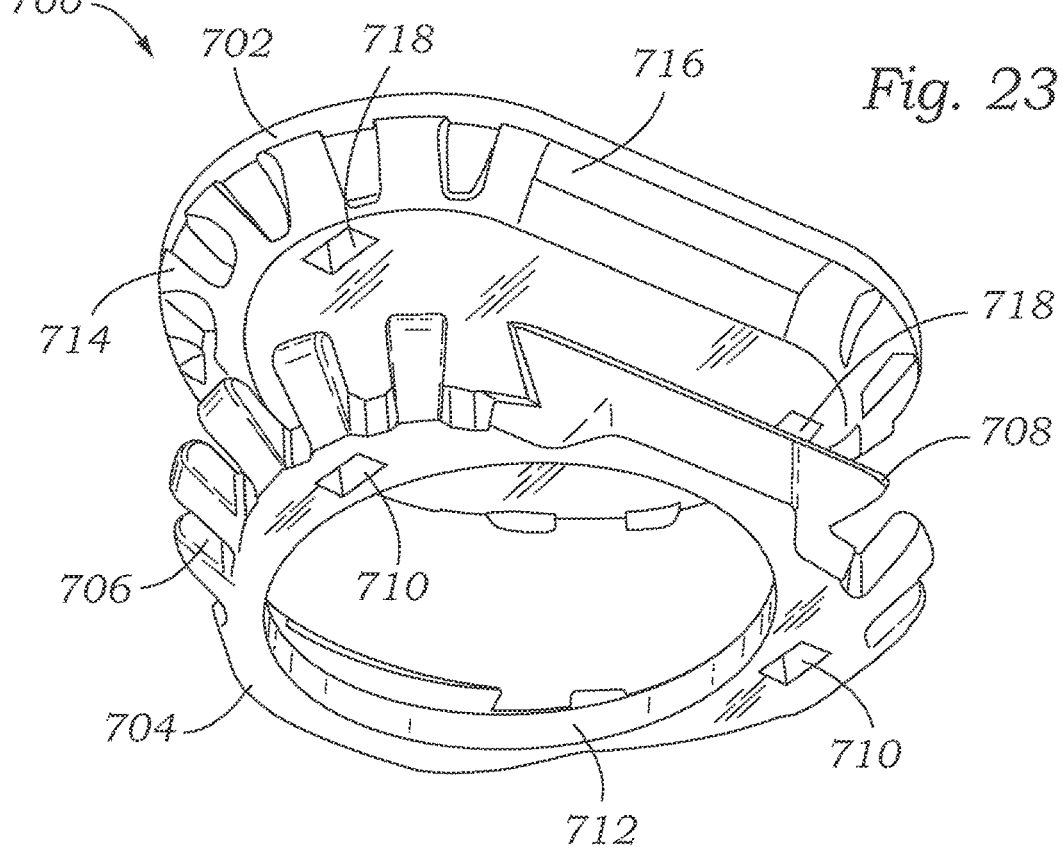
FIG. 23 shows another exemplary device including an atrial body and a one-piece ventricular body that are retained together such that claws of the ventricular body are positioned with recesses of the atrial body.

FIG. 23 shows another device 700 that is that is also similar to the device 500, except that the claws 706, 708 flare out more in a radially outward direction to engage with corresponding recesses 714, 716 disposed around the perimeter of the atrial portion 702. The recesses 714, 716 can be open radially outward in addition to downward, and can include a sloped engagement surface for receiving the flared claws 706, 708. The ventricular member 704 includes a central opening 712 with the plurality of claws 706, 708 disposed about the outer perimeter thereof. The atrial portion 702 can also include a central prosthetic valve structure (not shown) mounted between the recesses 714, 716. The retention members (not shown) attach to the ventricular portion 704 at features 710 and attach to the atrial portion 702 at corresponding features 718.

As the atrial and ventricular portions 702, 704 are drawn together from opposite sides of the native mitral valve, the claws 706, 708 engage the native annulus and/or leaflets and push the tissue into the recesses 714, 716. This forces the native valve tissue to assume a tortuous path around the tips of the claws within the recesses, providing improved sealing and reduced paravalvular leakage. The registration between the claws and the recesses can also help guide the atrial and ventricular portions together in proper alignment.

FIGS. 24-29 illustrate another exemplary device 300 that is configured to be implanted at the native mitral valve of the heart by clamping an atrial portion 320 (FIGS. 28-29) and a ventricular portion 302 (FIGS. 24-28) toward each other on opposite sides of the native mitral valve. The atrial and ventricular portions 320, 302 can be pulled towards each other, compressing and clamping the native mitral valve therebetween. Retention members 332 (FIG. 28) pass through the mitral valve orifice, coupling the atrial and ventricular members 320, 302 together and clamping the native mitral valve anatomy.

FIGS. 24 and 25 show the ventricular member 302 with a removable handle 304 attached. The ventricular member 302 forms a generally D-shaped ring with a gap or break 306. The ventricular member 302 can include a flat or straight side 308 and an arcuate side 310 with the break 306 at one corner between the flat side and the arcuate side. The break 306 can alternatively be located anywhere around the ring. The D-shape is configured to generally conform to a natural shape, or a desired reconfigured shape, of the native mitral valve. The handle 304 can attached to the ventricular member 302 at any location around the ring, such as at the flat side 308, as illustrated. The handle 304 can extend through the middle of the ring and curve back up to attach to a lower side of the ring, as illustrated, in some embodiments. The handle 304 can be attached to the ventricular member 302 in an easily releasable manner, such as with sutures, magnetically, or a snap fit. After implantation of the ventricular member 302, the handle 304 can be detached and removed.

Figure 26:
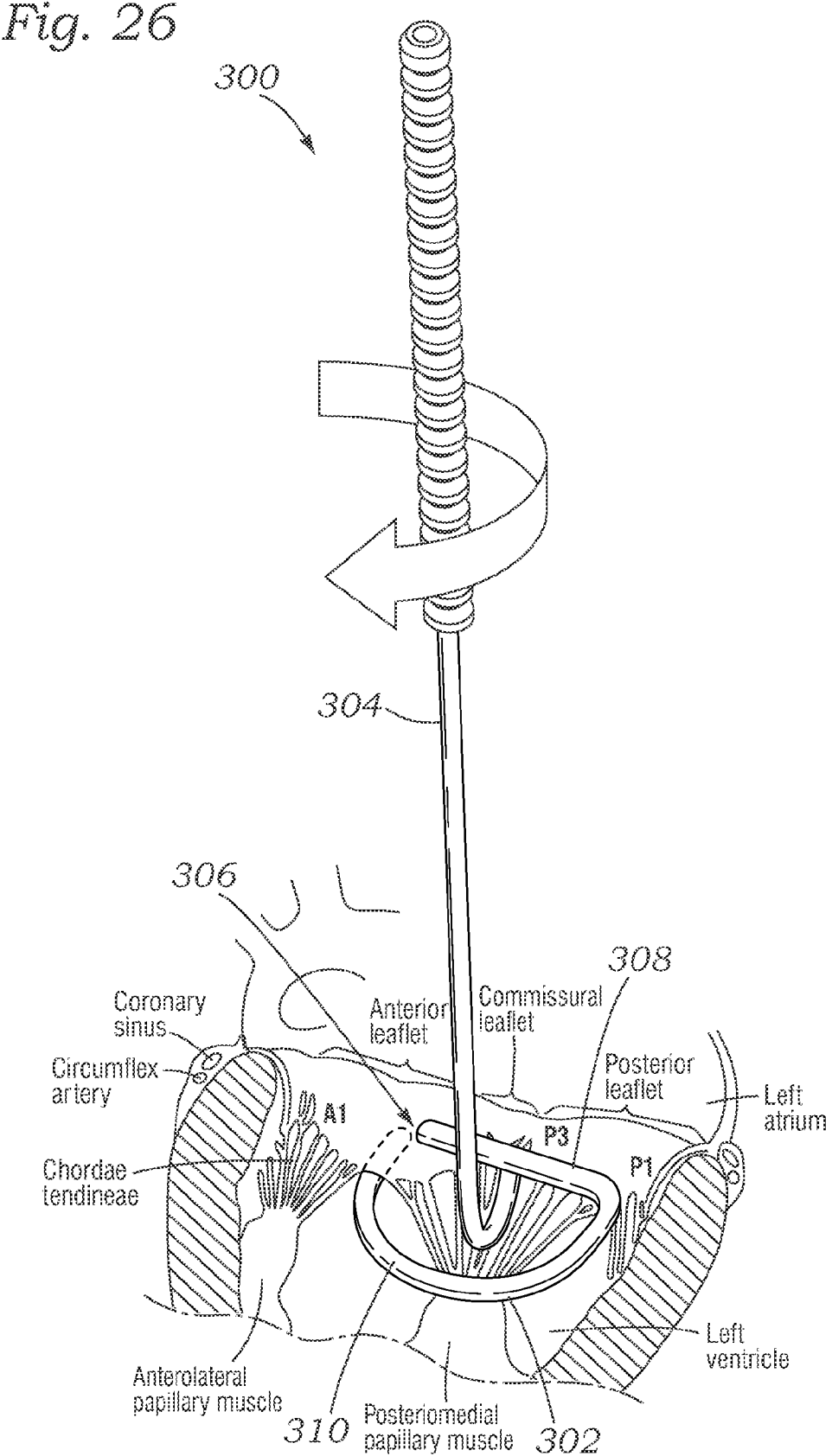
FIG. 26 illustrates a method of positioning the ventricular member of FIG. 24 around the native mitral valve leaflets and chordae.
Figure 27:
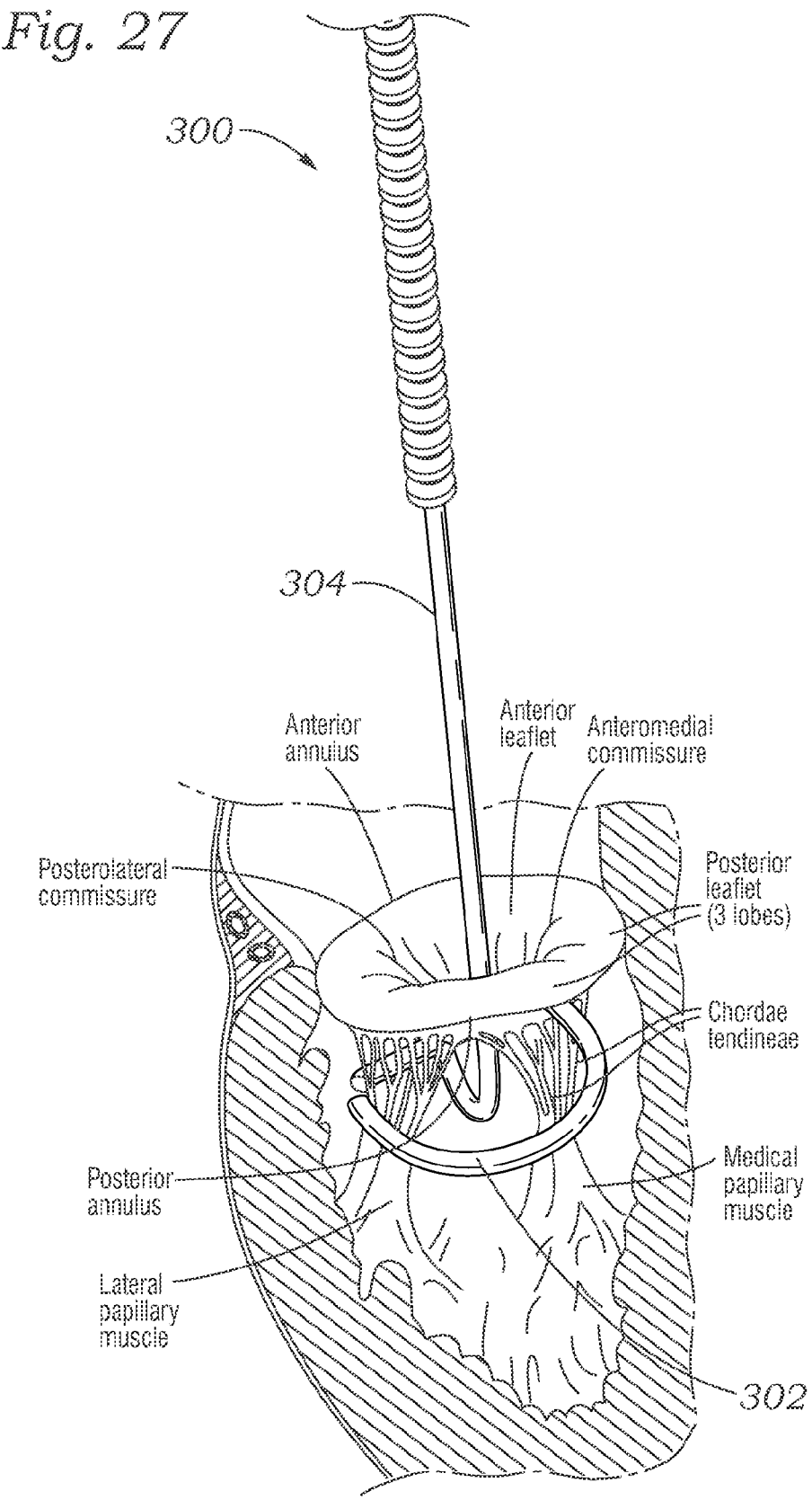
FIG. 27 shows the ventricular member of FIG. 24 positioned around the native mitral valve leaflets and chordae.

FIG. 26 shows an exemplary method of positioning the ventricular member 302 around and behind the native mitral leaflets and chordae within the left ventricle. FIG. 27 shows an exemplary configuration with the ventricular member 302 positioned fully around and behind the native mitral leaflets and chordae within the left ventricle. As shown in FIG. 26, a free edge of one of the native leaflets can be directed into the break 306 in the ventricular member 302. In FIG. 26, the A2 region of the anterior mitral leaflet is initially inserted through the break 306. In other methods, the P2 region of the posterior leaflet, or any other free edge of the leaflets, can be initially inserted through the break 306. As the user rotates the handle 304 as shown by the arrow around the handle in FIG. 26, the arcuate side 310 of the ventricular member 302 moves behind and around the native leaflets and chordae. The ventricular member 302 can rotate generally around the longitudinal axis of the handle 304. After about 360 degrees of rotation, all or most of the ventricular member 302 is positioned behind the native leaflets and chordae, as shown in FIG. 27. The ventricular member 302 can be resiliently flexible such that it can deform to some extent as it is directed around the native structure.

Figure 28:
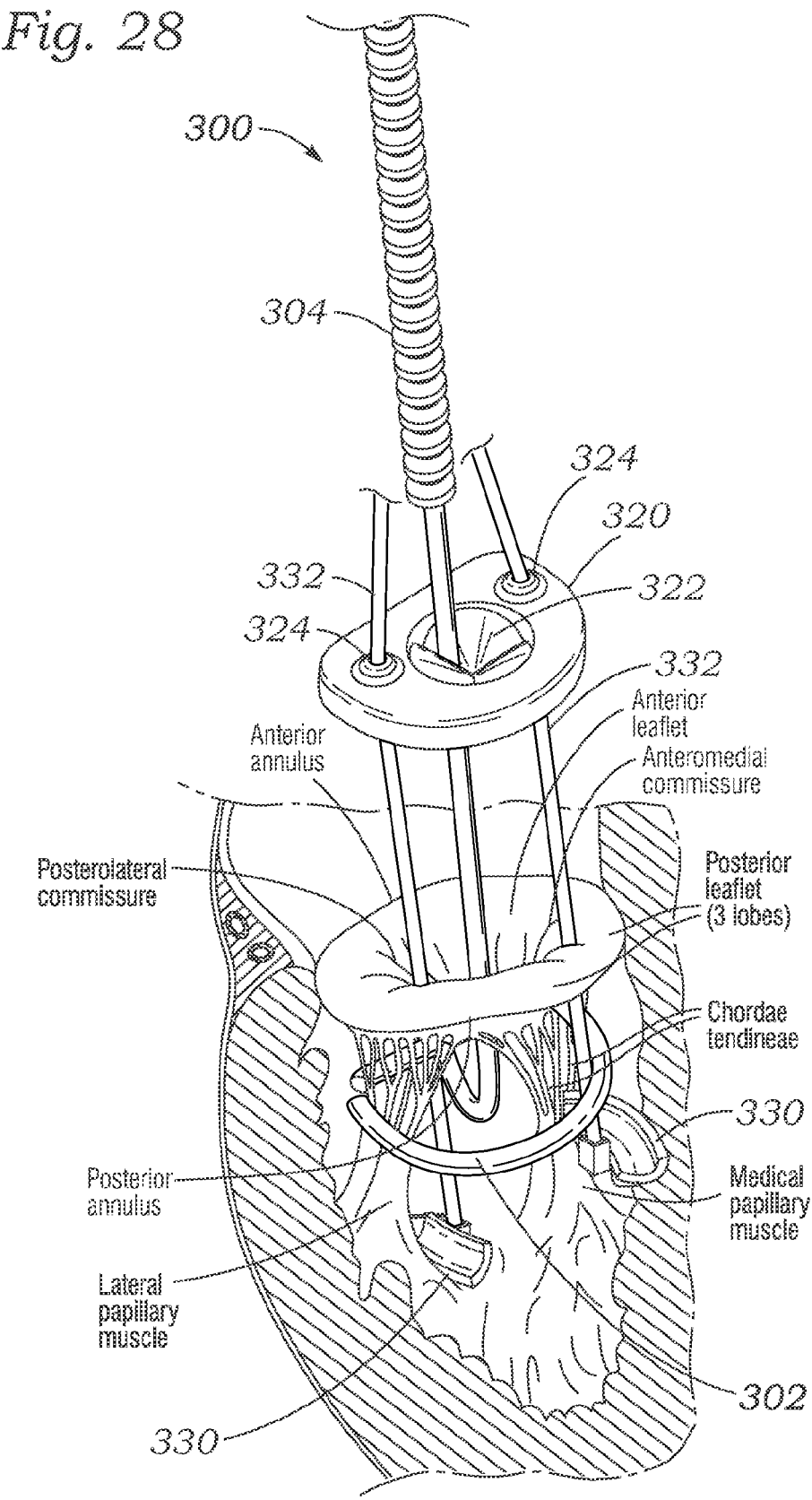
FIG. 28 shows the ventricular member of FIG. 24 positioned around the native mitral valve leaflets and chordae, an atrial portion including a prosthetic valve advanced over the releasable handle, and retention members extending down from the atrial portion, through the native valve orifice, and through the ventricular member.

FIG. 28 shows the atrial member 320 and the retention members 332 being introduced at the native mitral valve after the ventricular member 302 has been positioned around the native leaflets and chordae. The atrial member 320 includes a central valve structure 322, which can include a prosthetic leaflet valve and two locking mechanisms 324

(e.g., ratcheting mechanisms) through which the retention members 332 pass. The atrial member 320 can have a D-shape that corresponds to the shape of the ventricular member 302. The atrial member 320 can be lowered over the handle 304 to bring it near to the ventricular member 302 on the atrial side of the native annulus.

The retention members 332 pass through the native mitral valve orifice and through the ventricular member 302 and include engagement members 330 at the ventricular ends. The engagement members 330 can be cupped, include claws or tines, or otherwise shaped to engage around the ventricular member 302 and/or native anatomy when the retention members 332 are pulled tight. As shown, the engagement members 330 can be located to engage with the arcuate side 310 of the ventricular member 302 near the commissures of the native mitral valve.

In alternative embodiments, a single engagement member can be used instead of two or more as shown in FIG. 28. Such a single engagement member can comprise a fully or partially annular trough that engages around the lower side of the ventricular member 302. In some embodiments, such a single engagement member may be resiliently deformable such that it can be deformed to fit through the ventricular member 302 from the atrial side and then allowed to resiliently revert to its operative shape in the left ventricle.

Figure 29:
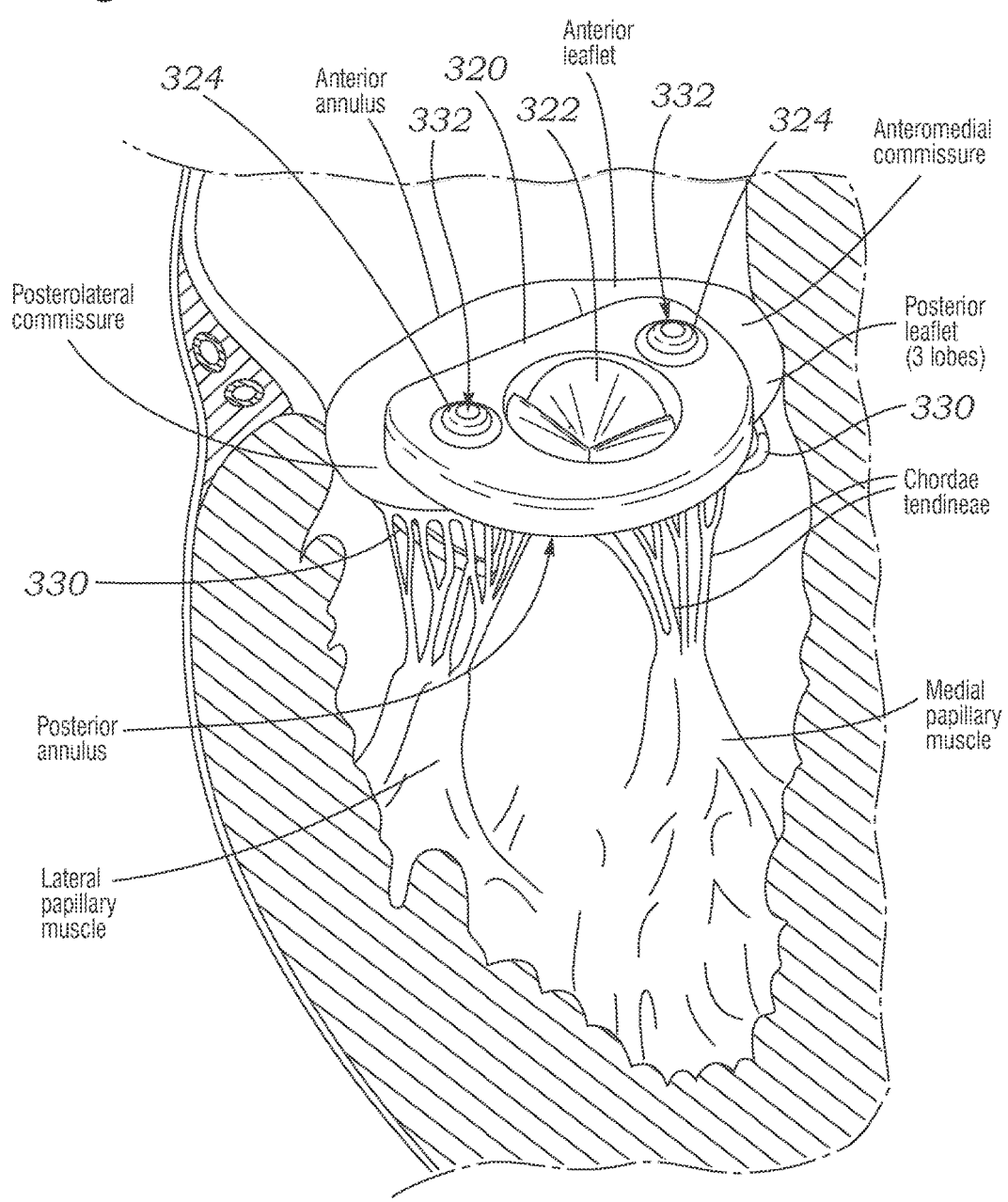
FIG. 29 shows the atrial member and ventricular of FIG. 28 member retained to the native mitral valve using the retention members of FIG. 28.

From the position shown in FIG. 28, the free ends of the retention members 332 can be pulled through the locking mechanisms 324 in the atrial member 320 to draw the engagement members 330 against the ventricular member 302 and pull the ventricular member 302 toward the atrial member 320. The atrial member 320 can be pushed downwardly along the retention members until it engages the atrial side of the native valve structure. FIG. 29 shows the ventricular member 302 drawn tightly toward the atrial member 320 with the native valve structure sandwiched therebetween. The engagement members 330 can be located at an area between the native chordae in some methods, while in other methods the native chordae can become pinched between the engagement members 330 and the ventricular member 302. For example, the native annulus and/or leaflets can become pinched between the upper side of the ventricular member 302 and the lower side of the atrial member, while the leaflets and/or chordae can loop around the inner side of the ventricular member 302 and be pinched between the lower side of the ventricular member 302 and the upper side of the engagement members 330. This tortuous path imposed on the native structure can help improve the paravalvular seal, reducing paravalvular leakage.

Once the retention members 332 have been desirable tightened, the handle 304 can be detached from the ventricular member 302 and removed through the prosthetic valve 322, and the free ends of the retention members can be optionally cut off, as shown in FIG. 29. In this implanted configuration, the device 300 can clamp securely onto the native mitral valve structure, for example, as shown in FIG. 29. The atrial member 320 can have an outer rim or lip that extends over the perimeter of the native annulus and/or a recessed area just inside of the outer rim or lip that receives the ventricular member 302 with the native structure trapped therebetween.

Figure 30:
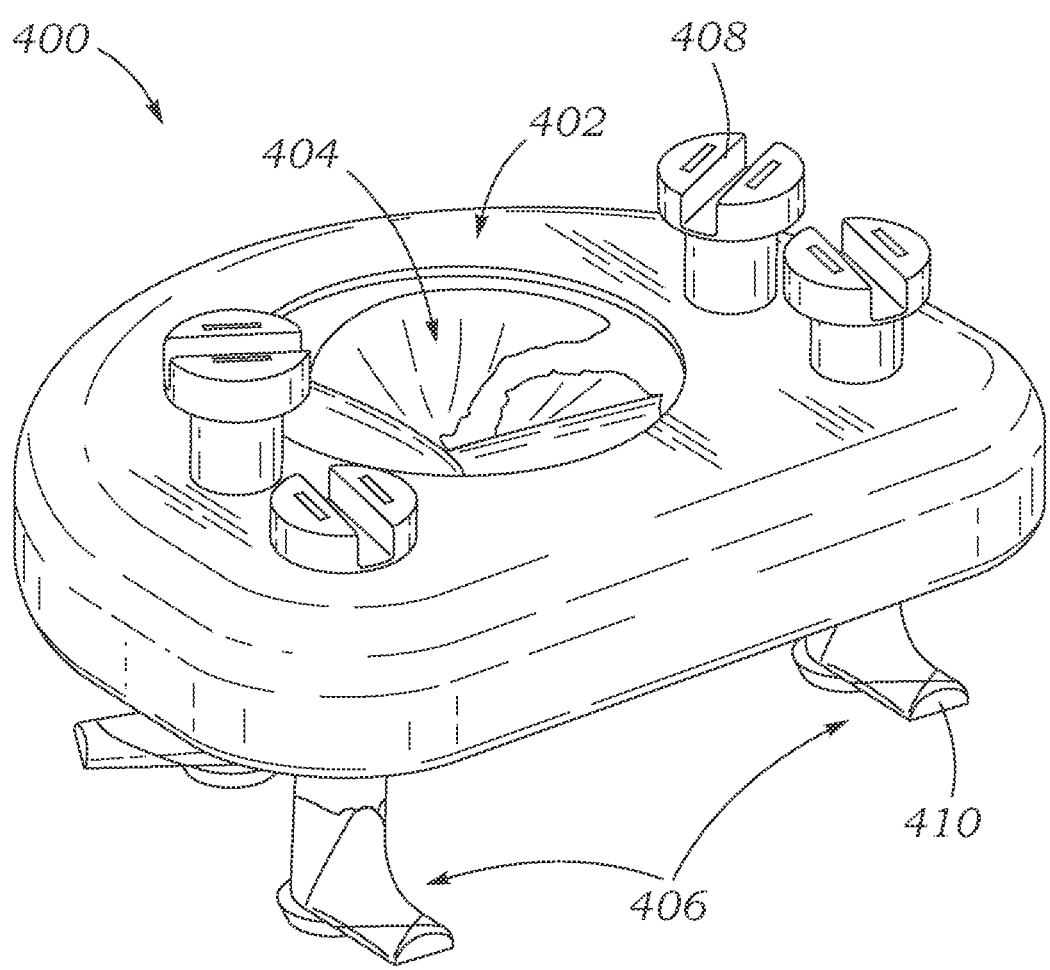
FIG. 30 shows another exemplary device including an atrial body housing a prosthetic valve structure and spring-biased retention members mounted to the atrial body.

FIG. 30 shows another exemplary device 400 that is configured to be implanted at the native mitral valve of the heart by disposing the device 400 and a D-shaped ring, for example, the ventricular portion 302 of FIGS. 24-25, on opposite sides of the native mitral valve, and by drawing the device 400 and D-shaped ring towards each other, thereby clamping native mitral valve tissue therebetween. The following discussion describes the use of the device 400 in conjunction with the ventricular portion 302 illustrated in FIGS. 24-25; however, those skilled in the art will understand that the device 400 is also compatible with other D-shaped rings. The device 400 includes a D-shaped atrial body 402 having a central prosthetic valve 404 that can be passed over the handle 304, or the like, after the ventricular portion 302 has been positioned behind and around the native leaflets and chordae. The atrial body 402 and ventricular portion 302 can be held in compression with retention members 406, clamping the native mitral valve between the atrial body 402 and the ventricular portion 302. Retention members 406 are mounted in the atrial body 402 and pass through the mitral valve orifice into the left ventricle, where they engage the ventricular portion 302 to secure the ventricular portion to the atrial body, thereby clamping the prosthetic valve to the native mitral valve anatomy.

Each of the retention members 406 includes a hook 410 that can be rotated between a first position in which the ventricular portion may be positioned around the retention members and a second position in which the hooks 410 extend under the ventricular portion 302 and hold it in compression. The retention members 406 include heads 408 positioned above the atrial body 402 that are engageable by the user for rotation of thereof, for example, including one or more slots or indentations (e.g., for receiving a suitable tool) and/or including one or more friction enhancing surfaces (e.g., suitable for manual manipulation). The retention members 406 can further include springs or other biasing mechanism (not shown) mounted between the upper surface of the atrial body 402 and the lower surfaces of the heads 408. Such springs can bias the retention members 406 in the atrial direction relative to the atrial body 402.

The retention members 406 can initially be rotated so that the hooks 410 point inwardly and/or circumferentially so that the hooks can be inserted through the ventricular portion 302. Each retention member 406 can then be depressed relative to the atrial body 402, compressing the spring, to move the hook 410 down through the ventricular portion 302. With the hook 410 positioned below the level of the ventricular portion 302, the user can rotate the head 408 with the spring still compressed to move the hook 410 underneath the ventricular portion and then release the spring. The hook 410 then contacts and engages the lower surface of the ventricular portion 302 and pulls the ventricular portion and the atrial body 402 toward each other on opposite sides of the native valve structure under the biasing force of the spring. The device 400 can eliminate the need to pull the retention members up through the atrial body, can provide a pre-selected degree of retention force, and can avoid the need to cut off the excess free ends of the retention members after implantation.

FIGS. 31-34 show another exemplary device 800, similar to the device 400 in FIG. 30, that is configured to be implanted at the native mitral valve of the heart by disposing the device 800 and a D-shaped ring on opposite sides of the native mitral valve, and by drawing the device 800 and D-shaped ring towards each other, thereby clamping native mitral valve tissue therebetween. The following discussion describes the use of the device 800 in conjunction with the D-shaped ventricular portion 302 illustrated in FIGS. 24-25; however, those skilled in the art will understand that the device 800 is also compatible with other D-shaped rings. The device 800 includes a D-shaped atrial body 802 having a central prosthetic valve 804. The device 800 can be passed over a handle coupled to the ventricular portion 302 after the ventricular portion has been positioned behind and around the native leaflets and chordae (as shown in FIGS. 27 and 35). The atrial body 802 and ventricular portion 302 can be held in compression with retention members 806, clamping the native mitral valve between the atrial body 802 and the ventricular portion 302. The atrial body 802 can include a groove 812 around the periphery that corresponds with the shape of the ventricular body 302 and helps to align the ventricular body with the atrial body when they are clamped together. The groove 812 also causes the compressed leaflet tissue to follow a more tortuous path to provide better sealing around the valve 804.

Retention members 806 are mounted in the atrial body 802 and pass through the mitral valve orifice into the left ventricle. The retention members 806 include an atrial head 808 and a ventricular hook 810. The hooks 810 engage the ventricular portion 302 to secure the ventricular portion tight against the native mitral valve tissue and the atrial body, thereby clamping the prosthetic valve 800 to the native mitral valve tissue.

Each of the retention members 806 can be rotated between a first position in which the hooks 810 can pass through the ventricular portion 302 and a second position in which the hooks 810 extend under the ventricular portion and hold it in compression. The retention member heads 808 are positioned above and/or in the atrial body 802 and can be engageable by the user for rotation of the hooks 810. The heads 808 can include, for example, one or more slots or indentations (e.g., for receiving a suitable tool) and/or including one or more friction enhancing surfaces (e.g., suitable for manual rotation). The device 800 can further include springs or other biasing mechanism (e.g., spring 816 in FIG. 36) mounted between the atrial body 802 and the retention members 806. Such springs can bias the retention members 806 in the atrial direction relative to the atrial body 802.

The heads 808 can initially be rotated so that the hooks 810 point inwardly and/or circumferentially so that the hooks can be inserted through the ventricular portion 302. With the atrial body 802 and the ventricular member 302 held in compression across the mitral valve, each head 808 can be depressed relative to the atrial body 802, resiliently deforming (e.g., compressing or elongating) the spring, to move the hooks 810 down through the ventricular portion 302. The user can then rotate each head 808 with the spring still resiliently deformed to move the hook 810 underneath the ventricular portion 302, and then release the head 808 to allow the spring to exert a clamping force. The spring causes the hook 810 engage the lower surface of the ventricular portion 302 and urge the ventricular portion and the atrial body 802 toward each other on opposite sides of the native valve tissue. The spring can comprise a coil spring, leaf spring, compressible or stretchy material (e.g., a foam), and/or any other resiliently deformable material. In some embodiments, the spring can be positioned between the head 808 and the atrial body 802 so that the spring is resiliently shortened or compressed when the head is pressed down relative to the atrial body. In some embodiments, the spring can be positioned between the hook 810 and the atrial body 802 so that the spring is stretched or tensioned when the head 808 is depressed.

FIG. 36 is schematic representation of an embodiment including a spring 816 that is elongated and tensioned when the hook 810 of the retention member 806 is engaged under the ventricular member 302 with the leaflet 822 pinched therebetween. In the FIG. 36, the ventricular member 302 is positioned under the annulus 824 adjacent the ventricular wall 820 with the proximal portion of the leaflet, or the annulus, 824 pinched between the atrial body 802 and the ventricular body 302.

The device 800 can include any number of retention members 806. In some embodiments, just single retention member is included. In some embodiments, two, three or more retention members are included.

The hooks 810 can have any shape. In some embodiments, the hooks are generally flattened plates that extend generally perpendicular to the atrial-ventricular axis. In some embodiments, the hooks 810 can include curvature so that they extend up around the ventricular member in the atrial direction. In some embodiments, the hooks 810 can include a tapered or gradually changing thickness profile to that the compression force on the ventricular body increases gradually as the hooks are rotated. In some embodiment, the hooks can include a notch or recess into which the ventricular member snaps into or is held in to keep the hooks from disengaging accidentally. In some embodiments, the hooks can be straightened to point generally ventricularly to pass through the ventricular member, and the hooks can then curl up or actuate to a more perpendicular position under the ventricular member. In some embodiments, the hooks can include a barbed structure so that the hooks deflect as the pass through the ventricular member and then snap out under the ventricular member as the clear the bottom of the ventricular member. In some embodiments, the ventricular member can include a positive engagement feature that receives and retains the hooks or another part of the retention members. In some embodiments, magnets can be used to secure the retention members to the ventricular members.

The device 800 can eliminate the need to pull the retention members up through the atrial body, can avoid the need to cut off the excess free ends of the retention members after implantation, and/or can provide a pre-selected degree of retention force.

In any of the embodiments described herein, and similar embodiments, after the atrial and ventricular portions of the implant have been drawn together and desirably tightened using the described ratcheting mechanisms and/or other retention members, the free ends of the retention members that extend past the ratcheting mechanisms or other locking mechanism can be removed, such as by cutting them off.

In alternative embodiments, one or more ventricular portions/members can be magnetically retained or secured to one or more atrial portions/members. In such embodiments, retention members physically extending through the native mitral valve are optional. The one or more atrial members can include one or more magnets or magnetic material, and/or the one or more ventricular members can include one or more magnets or comprise magnetic material. In some embodiments, the atrial member includes one or more magnets or includes magnetic material, and the ventricular member includes or comprises a ferrous metal, a ferromagnetic material, and/or other magnetically attracted material that is attracted to the one or more magnets or magnetic material of the atrial member. In other embodiments, the ventricular member include magnets or magnetic material and the atrial member includes or comprises a ferrous metal, and ferromagnetic material, and/or other magnetically attracted material that is attracted to the magnets or magnetic material of the one or more ventricular members. The native leaflets and/or annulus can be trapped between the magnets/magnetic material such that the atrial member need not be directly, physically coupled to the ventricular member(s).

Any of the embodiments and methods described herein, including those described as prosthetic mitral valves or in relation to the native mitral valve, can, where practicable, be alternatively implanted at other native heart valve locations, such as at the native tricuspid or aortic valve locations. Some embodiments of implantations at other heart valve locations include one or more minor alterations to the devices, methods, and systems disclosed herein, such as implanting the device 180° compared with the orientation illustrated herein, adjusting the number and/or locations of retention members or hooks, and/or adjusting the shape of the ventricular ring or peripheral rim around the prosthetic valve structure to accommodate a differently shaped valve annulus. Use at other native valve sites may also include excising parts or all of the native valve leaflets.

While many different embodiments are individually described herein, any of the features, properties, and related methods of use that are described in relation to any one or more of these embodiments can also be included, used, or applied in an analogous manner with any other embodiments described herein, to the extent practicable.

As used herein, the singular terms "a", "an", and "the" include plural referents unless context clearly indicates otherwise. The term "comprises" means "includes without limitation." The term "coupled" means physically linked and does not exclude intermediate elements between the coupled elements. The term "and/or" means any one or more of the elements listed. Thus, the term "A, B, and/or C" means "A", "B", "C", "A and B", "A and C", "B and C", or "A, B, and C".

Although methods and devices similar or equivalent to those described herein can be used in the practice or testing of the present technology, only certain suitable methods and devices are described herein. The methods, and devices, and features described herein are illustrative only and not intended to be limiting.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim at least all that comes within the scope of the following claims.

The invention claimed is:

1. A prosthetic mitral valve comprising:
an atrial portion for placement in the left atrium;
a ventricular portion for placement in the left ventricle; and
one or more retention members that couple the atrial portion to the ventricular portion;
wherein the atrial portion includes a prosthetic valve structure;
wherein the ventricular portion is configured to be implanted under the native mitral valve annulus and behind the native mitral valve leaflets with the native mitral chordae tendineae intact;
wherein the atrial portion and the ventricular portion are configured to become engaged on opposite sides of the native mitral valve annulus via the one or more retention members to anchor the prosthetic mitral valve at the native mitral valve region;
wherein the one or more retention members include a spring-biasing mechanism; and
wherein the one or more retention members are mounted in the atrial portion such that a user can depress the retention members relative to the atrial portion, rotate the retention members to position a hook under the ventricular portion, and then release the retention members to allow the spring-biasing mechanism to cause the hook to engage the ventricular portion.

2. The prosthetic mitral valve of claim 1, wherein a length of the one or more retention members between the atrial portion and the ventricular portion is configured to shorten, thereby reducing a distance between the atrial portion and the ventricular portion.

3. The prosthetic mitral valve of claim 1, wherein the ventricular portion comprises a single ventricular member having a substantially annular shape and configured to be implanted under a majority of the circumference of the native mitral valve annulus.

4. The prosthetic mitral valve of claim 3, wherein the single ventricular portion member comprises a ring with a break at one location around a perimeter of the ring, the break being sized to allow a free edge of a native mitral valve leaflet to enter into the ring through the break.

5. The prosthetic mitral valve of claim 4, wherein the atrial portion includes a protrusion configured to be received by the break in the perimeter of the ventricular member for sealing the break.

6. The prosthetic mitral valve of claim 1, wherein the one or more retention members are mounted in the atrial portion such that the one or more retention members can be actuated by a user when the atrial portion and ventricular portion are brought together.

* * * * *